United States Patent
Mortishire-Smith et al.

(10) Patent No.: US 12,332,210 B2
(45) Date of Patent: Jun. 17, 2025

(54) TECHNIQUES FOR SAMPLE ANALYSIS USING PRODUCT ION COLLISION-CROSS SECTION INFORMATION

(71) Applicant: Waters Technologies Ireland Limited, Dublin (IE)

(72) Inventors: Russell Julian Mortishire-Smith, Macclesfield (GB); Hans Vissers, Breda (NL); Michael McCullagh, Northwich (GB)

(73) Assignee: Waters Technologies Ireland Limited, Dublin (IE)

( * ) Notice: Subject to any disclaimer, the term of this patent is extended or adjusted under 35 U.S.C. 154(b) by 368 days.

(21) Appl. No.: 17/795,658

(22) PCT Filed: Jan. 29, 2021

(86) PCT No.: PCT/IB2021/050733
§ 371 (c)(1),
(2) Date: Jul. 27, 2022

(87) PCT Pub. No.: WO2021/152538
PCT Pub. Date: Aug. 5, 2021

(65) Prior Publication Data
US 2023/0084362 A1    Mar. 16, 2023

(30) Foreign Application Priority Data
Jan. 29, 2020  (GB) ..................................... 2001249

(51) Int. Cl.
*G01N 27/622*    (2021.01)
*G16B 40/10*    (2019.01)
*H01J 49/00*    (2006.01)

(52) U.S. Cl.
CPC .......... *G01N 27/622* (2013.01); *G16B 40/10* (2019.02); *H01J 49/0036* (2013.01)

(58) Field of Classification Search
CPC ... G01N 27/622; G16B 40/10; H01J 49/0036; H01J 49/0027
(Continued)

(56) References Cited

U.S. PATENT DOCUMENTS

| 11,226,309 B2 * | 1/2022 | Richardson .............. G06N 3/02 |
| 2017/0076927 A1 * | 3/2017 | Green ................. H01J 49/0031 |
| 2018/0024108 A1 * | 1/2018 | Cooks ................... H01J 49/424 |
| | | 250/282 |

FOREIGN PATENT DOCUMENTS

| GB | 2527879 A | 1/2016 | |
| GB | 2562690 A * | 11/2018 | ........... G01N 27/622 |

(Continued)

OTHER PUBLICATIONS

Combined Search and Examination Report for United Kingdom Patent Application No. GB2101249.7, mailed Jul. 8, 2021.

(Continued)

*Primary Examiner* — Michael Maskell
(74) *Attorney, Agent, or Firm* — Goodwin Procter LLP

(57) ABSTRACT

Techniques and apparatus for determining atomic-level configurations of product ions are described. In some embodiments, product ion CCS information may be used to determine substructural configurations of product ions, such as isomers. For example, in one embodiment, an apparatus may include at least one memory and logic coupled to the at least one memory to: receive analytical information for a plurality of product ions, the analytical information comprising product ion collision cross-section (CCS) information, for at least one product ion of the plurality of product ions, determine a variance value of the product ion CCS information. Other embodiments are described.

14 Claims, 29 Drawing Sheets

(58) Field of Classification Search
USPC .................................................. 250/281, 282
See application file for complete search history.

(56) References Cited

FOREIGN PATENT DOCUMENTS

| WO | 2017036545 | A1 |   | 3/2017  |             |
|----|------------|----|---|---------|-------------|
| WO | 2018005948 | A1 |   | 1/2018  |             |
| WO | 2019240289 | A1 |   | 12/2019 |             |
| WO | WO-2019229723 | A1 | * | 12/2019 | ........... G01N 27/623 |

OTHER PUBLICATIONS

Examination Report for United Kingdom Patent Application No. GB2101249.7, mailed Feb. 23, 2022.
International Search Report and Written Opinion for International Patent Application No. PCT/IB2021/050733, mailed Apr. 19, 2021.
McCullagh, M., et al., "Use of ion mobility mass spectrometry to enhance cumulative analytical specificity and separation to profile 6-C /8-•• glycosylflavone critical isomer pairs and known-unknowns in medicinal plants", Phytochemical Analysis, 30(4):424-436, Mar. 19, 2019.
McCullagh, M., et al., "Profiling of the known-unknown Passiflora variant complement by liquid chromatography—Ion mobility—Mass spectrometry", Talanta, Elsevier, Amsterdam, NL, 221:XP086294900, Jul. 23, 2020.
International Preliminary Report on Patentability for International Patent Application No. PCT/IB2021/050733, mailed Aug. 11, 2022.

* cited by examiner

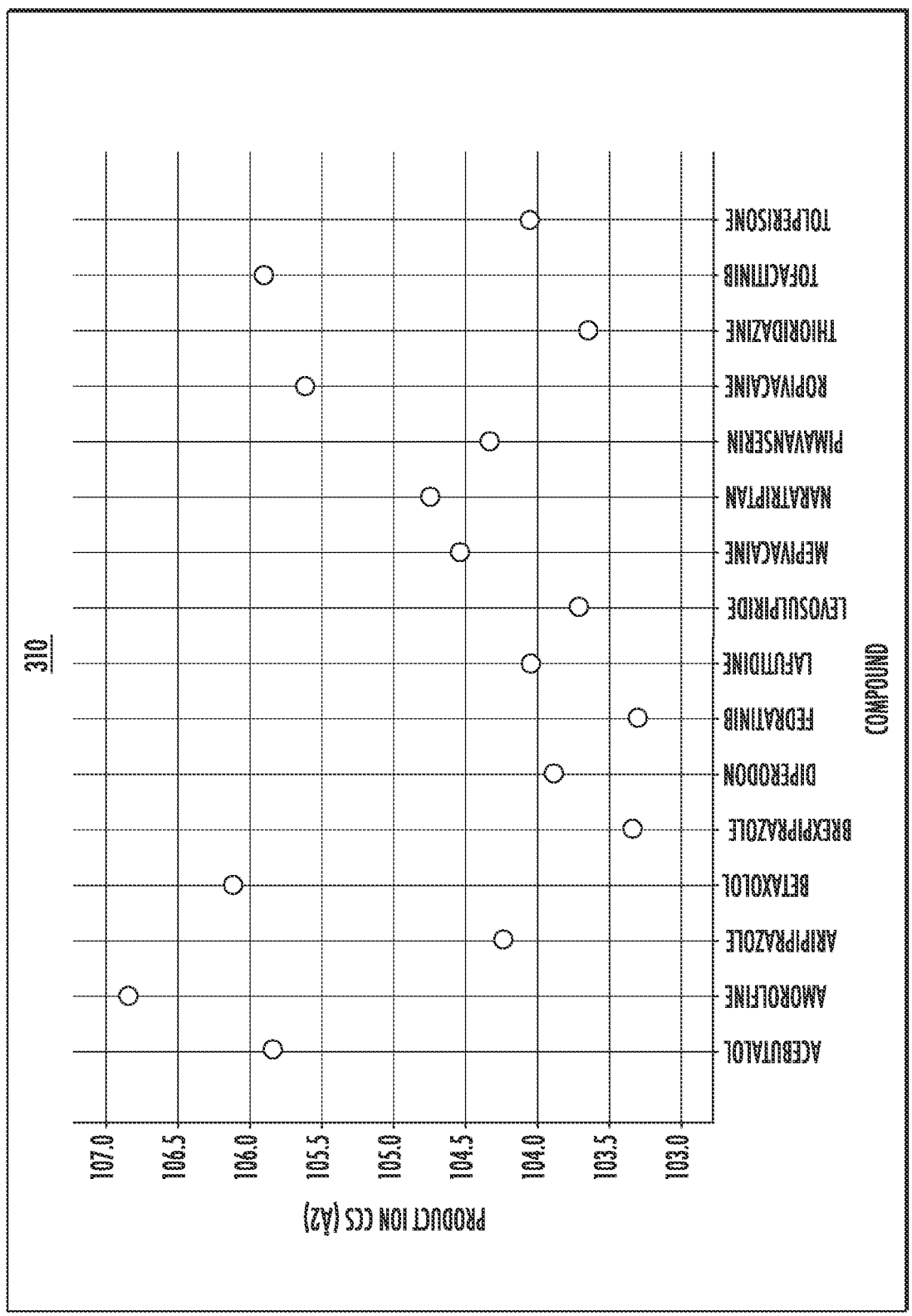

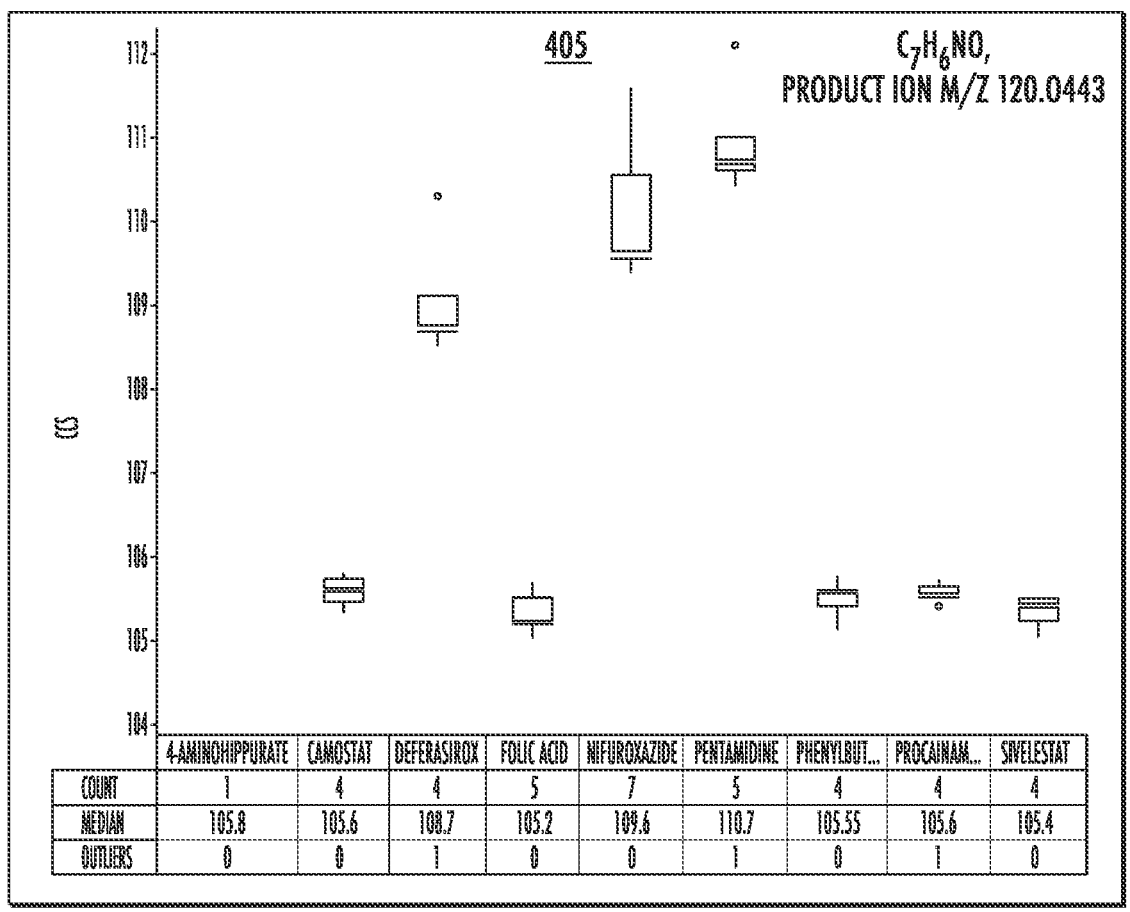
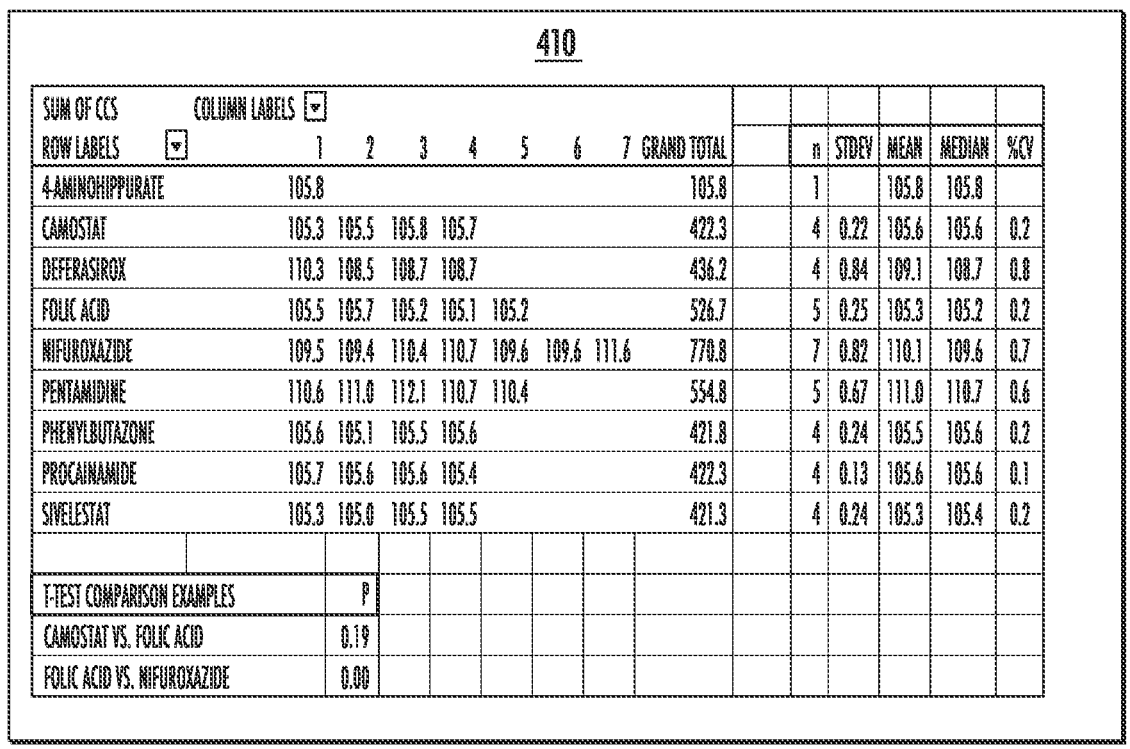
FIG. 4A

| MOLECULE | EXPECTED FRAGMENT | PREDICTED PRODUCTION CCS | EMPIRICAL PRODUCTION CCS | %CV |
|---|---|---|---|---|
| TERFENADINE | TERFENADINE - 203 | 148.8 | 145.6 | 2.2% |
| | TERFENADINE - 262 | 164.2 | 167.2 | -1.8% |
| | TERFENADINE - 280 | 168.2 | | |
| | TERFENADINE - 436 | 225.2 | 224.2 | 0.5% |
| | TERFENADINE - 454 | 223.2 | 226.5 | -1.5% |
| | TERFENADINE - 472 | 228.1 | 231.9 | -1.7% |
| | | | RMSD | 1.6% |

TECHNIQUES FOR SAMPLE ANALYSIS USING PRODUCT ION COLLISION-CROSS SECTION INFORMATION

CROSS-REFERENCE TO RELATED APPLICATION

This application is a U.S. national phase filing claiming the benefit of and priority to International Patent Application No. PCT/IB2021/050733, filed Jan. 29, 2021, which claims priority from and the benefit of United Kingdom Patent Application No. 2001249.8, filed on Jan. 29, 2020. The entire contents of these applications are incorporated herein by reference.

TECHNICAL FIELD

Embodiments herein generally relate to mass analysis of samples, and, more particularly, to determining product ions obtained via fragmentation of one or more product ions based on collision-cross section (CCS) information of the product ions.

BACKGROUND

Conventional analytical techniques, such as mass spectrometry (MS), are not able to efficiently and accurately resolve low-level structural identification of components of a complex sample. For example, an MS spectrum may be used to determine the presence of a particular metabolite of a drug compound, but is insufficient to discern the presence and/or concentrations of specific isomers or other low-level characteristics of the metabolite. This challenge is particularly acute for product ions because, inter alia, processing mass analysis data for the fragments of precursor ions has been severely deficient or even non-existent for most classes of molecules. Accordingly, it is desired to provide techniques for resolving low-level structural characteristics of product ions of complex samples.

BRIEF DESCRIPTION OF THE DRAWINGS

FIG. 3B illustrates a graph of CCS versus m/z for product ions having the structure $C_6H_{12}N$ (m/z=98.096) according to some embodiments.

FIG. 4A illustrates a graph of CCS versus m/z for product ions having the structure $C_7H_6NO$ (m/z=120.0443) according to some embodiments.

FIG. 10 depicts empirical and predicted CCS information for Terfenadine according to some embodiments.

DETAILED DESCRIPTION

Figure 1:
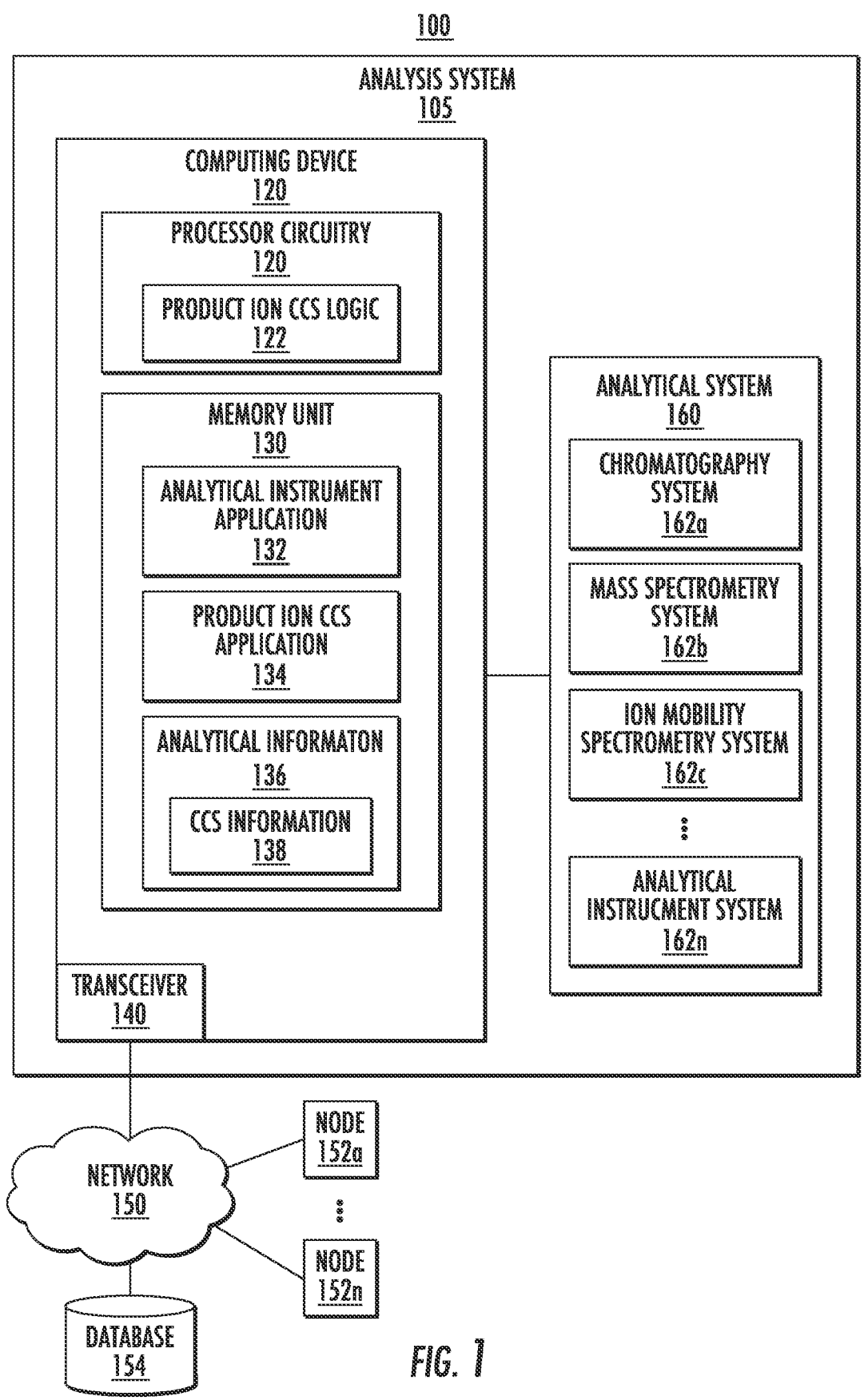
FIG. 1 illustrates an embodiment of a first operating environment.

Various embodiments may generally be directed toward systems, methods, and/or apparatus for determining components of interest of a sample and/or characteristics of the components using collision-cross section (CCS) or (Ω) information. In some embodiments, the components may include product ions generated via fragmentation of precursor ions of the sample. In various embodiments, CCS information of product ions may be determined and processed according to a product ion analysis process. In some embodiments, the product ion analysis process may use the product ion CCS information to determine atomic-level characteristics of the product ions. In some embodiments, substructural characteristics may include configurations of product ions that may otherwise have the same or substantially similar physiochemical characteristics, such as mass-to-charge (m/z) ratios. Non-limiting examples of atomic-level configurations may include isomer configurations, protomer configurations, and/or the like. Therefore, product ion analysis processes according to some embodiments may operate to determine substructural configurations (for instance, isomeric fragments) of product ions of a sample using product ion CCS information in combination with other mass analysis information, such as m/z, drift time (DT or $t_d$), retention time (RT or $t_r$), and/or the like.

Conventional techniques, such as MS methods, are not capable of differentiating certain structural variations in analyzed compounds. For example, mass spectrometry (MS) spectra may be used to determine the m/z of a compound, but may not be able to determine different isomers of a compound, with each isomer having the same m/z, especially for product ions. Therefore, other physiochemical information is required to differentiate the isomers. Accordingly, in some embodiments, a product ion CCS process may use product ion CCS information to discern different physicochemical configurations of product ions that may not be determined using conventional methods.

Mass spectrometer systems, such as system 205 of FIG. 2 described in more detail below, may operate to determine CCS information for product ions. However, product ion CCS has been poorly understood and defined within the analytical chemistry community. Therefore, use of product ion CCS information has been challenging and limited such that it has not meaningfully contributed to MS analysis tools. In addition, conventional techniques are not able to efficiently and accurately process product ion CCS data, particularly using certain methods, such as trap/transfer (TAP; Time-Aligned Parallel) fragmentation acquisition schemes.

For example, there has been a lack of an effective approach to connect product ions with their precursors using current software tools. A surrogate approach has been used that generates MS data (for instance, broadband DIA, ion mobility assisted DIA, and/or the like) data and determines product ions for all relevant components (for instance, pharmaceutical(s)) using DT correlation, that may be correlated to a look-up table. Trap fragmentation information may be obtained and split into different components componentized, for example, effectively as an MS1 or precursor data channel (as compared with a MS2 or product ion data channel). Observed product ions may be correlated with their CCS values with ions in the look-up table. However, even this approach is time consuming, inefficient, and requires specialized software tools that are not part of typical end-user MS systems.

Accordingly, some embodiments may provide multiple technological advantages over prior art systems. In addition, various embodiments may provide improvements in computing technology and technological features, for instance, by providing more effective and efficient processes for processing product ion CCS information to, among other things, determine characteristics of product ions and/or precursors of the product ions (for instance, isomer configurations). In a non-limiting technological advantage, a product ion CCS analysis process according to some embodiments may characterize unknowns (for instance, metabolites, pharmaceuticals, natural products, bio-markers, contaminants, and/or the like) to reduce a number of possible candidates of product ions in a sample (in one non-limiting example, via a library and/or look-up table of common product ions and their CCS values). In another non-limiting technological advantage, a product ion CCS analysis process according to some embodiments may provide improvements in CCS modeling and prediction over conventional methods (for instance, particularly with respect to three-dimensional (3D) descriptors), including, without limitation, CCS modeling and/or prediction using artificial intelligence (AI) and/or machine learning (ML) techniques. In an additional non-limiting technological advantage, a product ion CCS analysis process according to some embodiments may provide improvements in the specificity of product ion determinations (for instance, using two-dimensional (2D) product ion spectra). In a further non-limiting technological advantage, a product ion CCS analysis process according to some embodiments may be capable of using CCS-m/z fingerprinting (2D) and/or CCS-m/z-intensity (3D) to differentiate between compounds that are isomeric on a substructure (for instance, designer pharmaceuticals). Moreover, a non-limiting technological advantage may include a product ion CCS analysis process according to some embodiments that may use product ion CCS values in a priori structure determinations to reduce the number of possible candidates for a product ion (for instance, for natural products, extractables, leachables, contaminants, lipids, proteins, pharmaceuticals, and/or the like). Embodiments are not limited in this context. Other technological advantages are provided by the described embodiments.

Although some embodiments may use pharmaceuticals as an example, embodiments are not so limited as the processes described may be used to identify components in other experimental disciplines. Non-limiting examples may include drug impurity characterization, food speciation/storage analysis, chemical and (bio)pharmaceutical fingerprinting, biomedical research experiments, water/groundwater testing, soil testing, and/or the like.

Additional illustrative and non-limiting examples of uses of product ion CCS analysis processes according to some embodiments may include food and environmental applications, authentication, profiling, and/or the like, speciation, food ageing/storage/processing characteristics, pharmaceuticals (for instance, determining pharmaceutical fingerprint, profiling fingerprint for fake products, product purity, comparison to expected chemical fingerprint), biotransformation products, forensic toxicology and/or the like. Embodiments are not limited in this context.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage analytical data associated with analytical system 160. In some embodiments, analytical system 160 may include one or more analytical instrument systems 162*a-n* operative to perform mass analysis and/or other analysis processes on a sample. In various embodiments, analytical instrument systems 162*a-n* may be or may include a chromatography system, a liquid chromatography (LC) system, a gas chromatography (GC) system, a mass analyzer system, a mass spectrometer (MS) system, an ion mobility spectrometer (IMS) system, a high definition mass spectrometer (HDMS) system, a time-of-flight (ToF) MS system, an MS system operated in a data-dependent (DDA) mode, an MS system operated in a data independent (DIA), an MS system operated in a broadband DIA and/or ion mobility assisted DIA mode, a high-performance liquid chromatography (HPLC) system, a ultra-performance liquid chromatography (UPLC®) system, a ultra-high performance liquid chromatography (UHPLC) system, a solid-phase extraction system, a sample preparation system, combinations thereof, components thereof, variations thereof, and/or the like. In some embodiments, any of analytical instrument systems 162a-n may operate in combination. In exemplary embodiments, analytical system 160 may be or may include an analysis the same or substantially similar to analytical system 105 depicted in FIG. 1. Although LC, MS, LC-MS, MS/MS (tandem MS), IMS-MS, and HDMS$^e$ are used in examples in this detailed description, embodiments are not so limited, as other analytical instruments and/or operating modes capable of operating according to some embodiments are contemplated herein.

In some embodiments, analytical instrument systems 162a-n may operate to perform an analysis. For example, for an LC-MS system, analytical instrument systems 162a and 162b may operate to separate a sample and perform mass analysis on the separated sample to generate analytical information 136 that may include, for instance, spectra information, retention time, drift time, ion mobility information, CCS information 138, product ion CCS information 138, and/or the like. In another example, for an LC-MS-IMS system, analytical instruments 162a-c may operate to separate a sample and perform mass analysis and ion mobility analysis on a sample to generate analytical information 136 that may include, for instance, spectra information, $t_r$, CCS information (including product ion CCS information) 138, $t_d$ information, and/or the like. In some embodiments, analytical information 136 may include data from historical or database analyses, such as spectral databases, peptide libraries, protein libraries, standard reference material data, pharmaceutical databases (for instance, Food and Drug Administration (FDA) databases), drug interaction databases, metabolic databases, proteomic databases, and/or the like. Embodiments are not limited in this context.

In some embodiments, the CCS information 138 may include predicted CCS information and/or modeled CCS information. In some embodiments, CCS information 138 including product ion CCS information, may be combined with machine learning (ML) techniques, including, without limitation, artificial intelligence (AI) processes, neural networks, and/or the like. For example, product ion CCS information may be used in ML/AI applications to analyze, predict, model, or otherwise determine product ion characteristics, such as isomer structures of product ions obtained during an experiment. Product ion CCS information may be or may include product ion CCS computational models (e.g., ML processes, AI processes, neural networks (NNs), convoluted neural networks (CNNs), and/or the like. Embodiments are not limited in this context. In some embodiments, predicted precursor CCS values and/or modeled precursor CCS values may be used to reduce a number of candidates for review, annotation, identifications, and/or the like.

In various embodiments, analysis system 105 may include computing device 120 communicatively coupled to analytical system 162, one or more of analytical instrument systems 162a-n, and/or otherwise configured to receive and store analytical information 136. For example, analytical instrument 162b may operate to provide analytical data to a location on a network 150 (for instance, a cloud computing environment or analytical instrument management platform) accessible to computing device 120. In some embodiments, computing device 120 may be operative to control, monitor, manage, or otherwise process various operational functions of analytical system 160 and/or systems 162a-n thereof. For example, in various embodiments, computing device 120 may execute an analytical instrument application 132 operate to control various functions of one or more of analytical instrument systems 162a-n. For instance, analytical instrument application 132 may operate as a control interface for analyzing samples on analytical instrument systems 162a-n, receiving and/or processing analytical information from analytical instrument systems 162a-n, and/or the like. Non-limiting examples of analytical instrument applications 132 may include chromatography data software (CDS), mass spectrometry software, lab management software, LC-MS data analysis software, databases (for instance, mass spectral databases, proteomics databases, protein identification databases, and/or the like. Further illustrative and non-restrictive examples of analytical instrument applications 132 may include Empower™ (for instance, Empower™ 3) CDS, MassLynx™ Mass Spectrometry Software, Progenesis™ QI LC-MS data analysis software, and UNIFI™ scientific information system and/or variations or portions thereof developed by Waters Corporation of Milford, Massachusetts, United States of America. In some embodiments, software development kits (SDKs) and/or application programming interfaces (APIs) may be used by software platforms to access analytical instrument applications 132 and/or analytical data associated therewith. Embodiments are not limited in this context.

In some embodiments, computing device 120 may be or may include a stand-alone computing device, such as a personal computer (PC), server, tablet computing device, cloud computing device, and/or the like. In various embodiments, computing device 120 and/or portions or components thereof may be a component of one or more of analytical instrument systems 162a-n.

As shown in FIG. 1, computing device 120 may include processing circuitry 120, a memory unit 130, and a transceiver 140. Processing circuitry 120 may be communicatively coupled to memory unit 130 and/or transceiver 140. Processing circuitry 120 may include and/or may access various logic for performing processes according to some embodiments. For instance, processing circuitry 120 may include and/or may access product ion CCS logic 122. Processing circuitry 120 and/or product ion CCS logic 122, or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 2000. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although product ion CCS logic 122 is depicted in FIG. 1 as being within processing circuitry 120, embodiments are not so limited. For example, product ion CCS logic 122 may be located within an accelerator, a processor core, an interface, an individual processor die, implemented entirely as a software application (for instance, product ion CCS application 134) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store a product ion CCS application 134 that may, when executed by computing device 120, operate, alone or in combination with product ion CCS logic 122, to perform various processes according to some embodiments. For example, product ion CCS application 134 may generate CCS information 138, including product ion CCS information, stored locally in memory unit 130, database 154, and/or on a node 152a-n of network 150. Although product ion CCS application 134 and analytical instrument application 132 are depicted as separate applications (and/or logic) in FIG. 1, embodiments are not so limited. For example, product ion CCS application 134 may be a module or component of analytical instrument application 132 and vice versa.

In general, CCS information 138 may represent the effective area for the interaction between an individual ion and the neutral gas through which it travels. CCS may represent one type of physicochemical property and is related to chemical (sub)structure and three-dimensional conformation of an ion. In IMS, ions may be separated by their gas-phase transport in an electric field and will have different CCS values, which are dependent on their shape-to-charge ratio. In some embodiments, product ion CCS application 134 may use product ion CCS information to determine sample components, exclude potential candidates, and/or determine substructure characteristics of sample components (for instance, isomer configurations).

Figure 2:
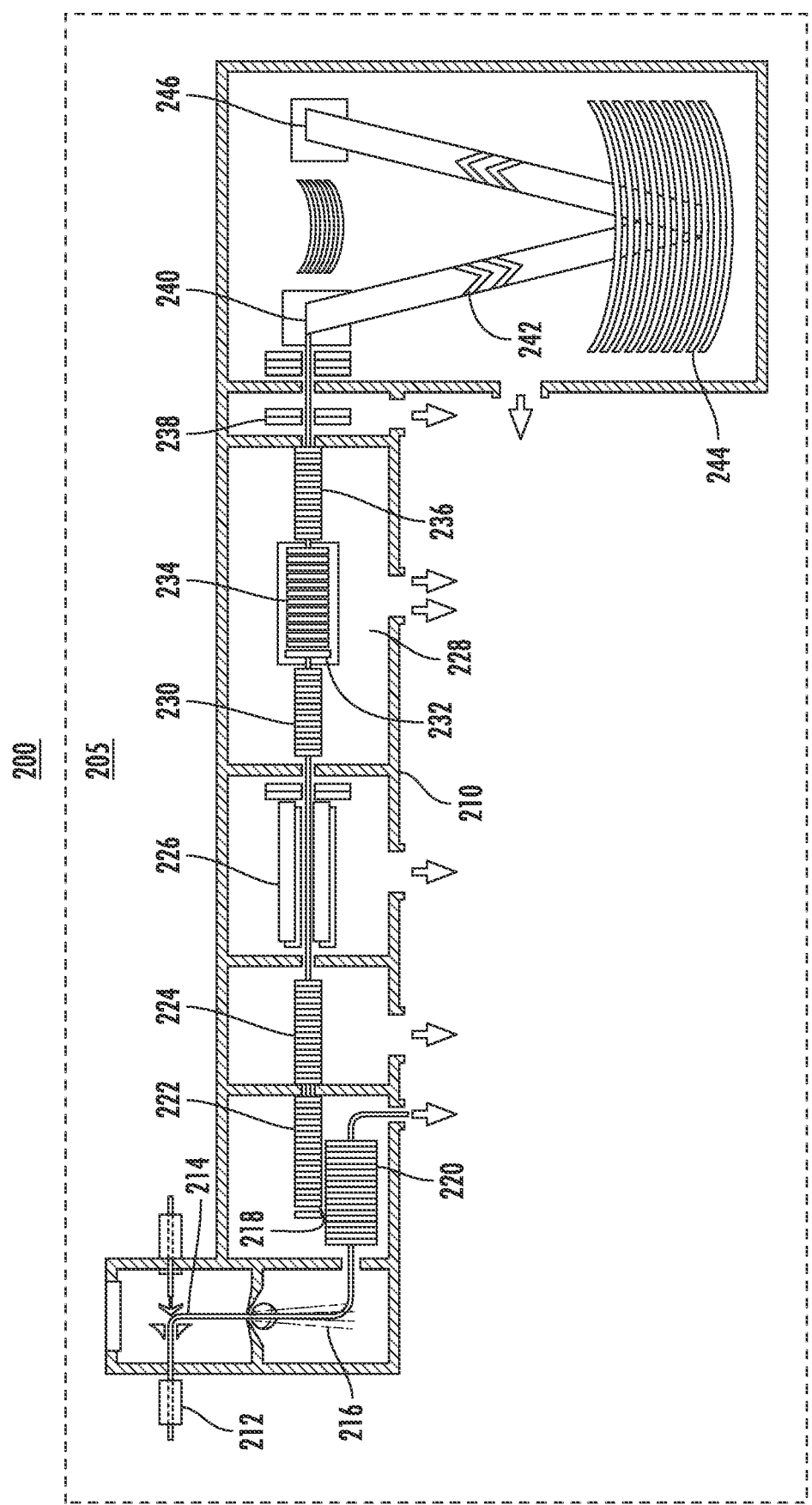
FIG. 2 illustrates an embodiment of a second operating environment.

FIG. 2 illustrates an example of an operating environment 200 that may be representative of some embodiments. As shown in FIG. 2, operating environment 200 may include an analysis system 205. In some embodiments, analysis system 205 may be a configuration of analysis system 160.

Analysis system 205 may include a mass spectrometer 210 suitable for use with various embodiments. A sample may be injected into mass spectrometer 210 at an injection inlet 212. The sample may be sprayed from a needle into an ionization chamber 214. Ionization of the sample may occur to form sample ions. The ionized sample may pass out of ionization chamber 214, and the ions may flow towards a first vacuum region 216. The sample may transfer through the first vacuum region into the stepwave ion guide 218. The stepwave ion guide 218 may then guide the ions along an ion guide initially in a large cross section area 220 and may then focus the ions into a smaller cross section in an off axis part 222 of the guide. The ions may then be transferred into a further ion guide 224, where the ions may be transmitted through to a quadrupole mass filter 226.

Quadrupole mass filter 226 may be used in a transmission mode, so that all the ions entering pass through the filter and into a Triwave chamber 228. Once the ions are passed into Triwave chamber 228 they may be collected in groups within a trap cell 230 of the Triwave chamber 228. A group of ions in trap cell 230 may then be released through a helium cell 232 and into an ion mobility separator 234. The ions may then temporally separate according to their ion mobility within ion mobility separator 234, and as ions exit the separator, they may be passed into a transfer cell 236 where ions of small ranges of ion mobility are collected in groups, and passed through transfer cell 236, several lenses 238, and into a ToF pusher region 240. Each group of ions of small mobility ranges can then be pulsed out of the ToF pusher region 240 into a flight tube 242 and into a reflectron 244, where they may be reflected back to a detection system 246, where the flight times of the ions are recorded, together with the small range of mobility of the ions.

A second, consecutive, analysis may then be performed along a similar basis, except, after the ions have been separated into the groups of small ranges of ion mobility in separator 234, energy may be provided to the ions within the transfer cell 236 to induce fragmentation of the ions in each group, to provide product or fragment ions. The product ions may be kept in the small groups according to the mobility of the parent ions, and may be passed into ToF pusher region 240. Similarly, each group of product ions from the precursor or parent ions of small mobility ranges can then be pulsed out of the ToF pusher region into a flight tube 242, into a reflectron 244, where they are reflected back to a detection system 246, where the flight times of these fragment ions are recorded, together with the small range of mobility of the precursor ions that produced the product ions.

In some embodiments, fragmentation may be performed within trap cell 230. In various embodiments, fragmentation may be performed within transfer cell 236. In some embodiments, fragmentation may be performed within trap cell 230 and transfer cell (for instance TAP (trap/transfer) fragmentation). In exemplary embodiments, IMS may be performed on product ions to generate product ion CCS information. For example, in some embodiments, fragmentation may be performed within trap cell 230 and IMS is performed on the resultant product ions.

According to some embodiments, IMS may be performed via analysis system 205 (or analysis system 160) under various conditions, such as gas type (for instance, nitrogen, helium, and/or the like), gas pressure, wave height, wave velocity, and/or other characteristics. In some embodiments, the IMS conditions may be varied to optimize CCS measurements and/or to increase variances between different conformations (for instance, isomers) of a compound of interest. For instance, a first gas type (or other condition) may be optimal for discerning isomers of compounds A-D, while a second gas type may be optimal for discerning isomers of compounds E-H. In another instance, a CCS value for a particular compound may be different depending on the gas type and/or other IMS condition.

Figure 3A:
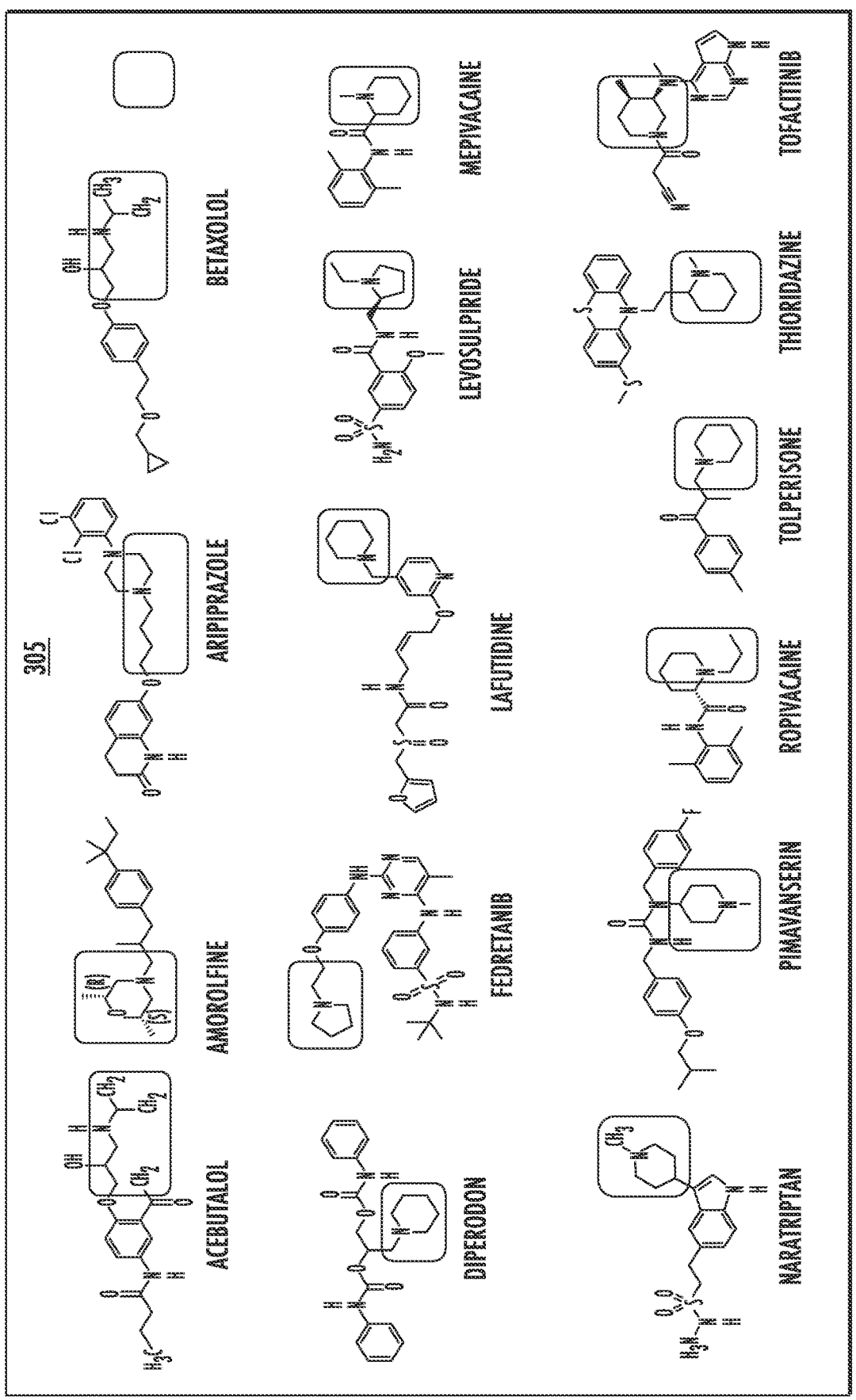
FIG. 3A illustrates precursor ions that may generate product ions having the structure $C_6H_{12}N$ (m/z=98.096).

FIG. 3A illustrates precursor ions that may generate product ions having the structure $C_6H_{12}N$ (m/z=98.096). For example, the bound region of the product ions may fragment to produce a product ion having the structure $C_6H_{12}N$.

Figure 3C:
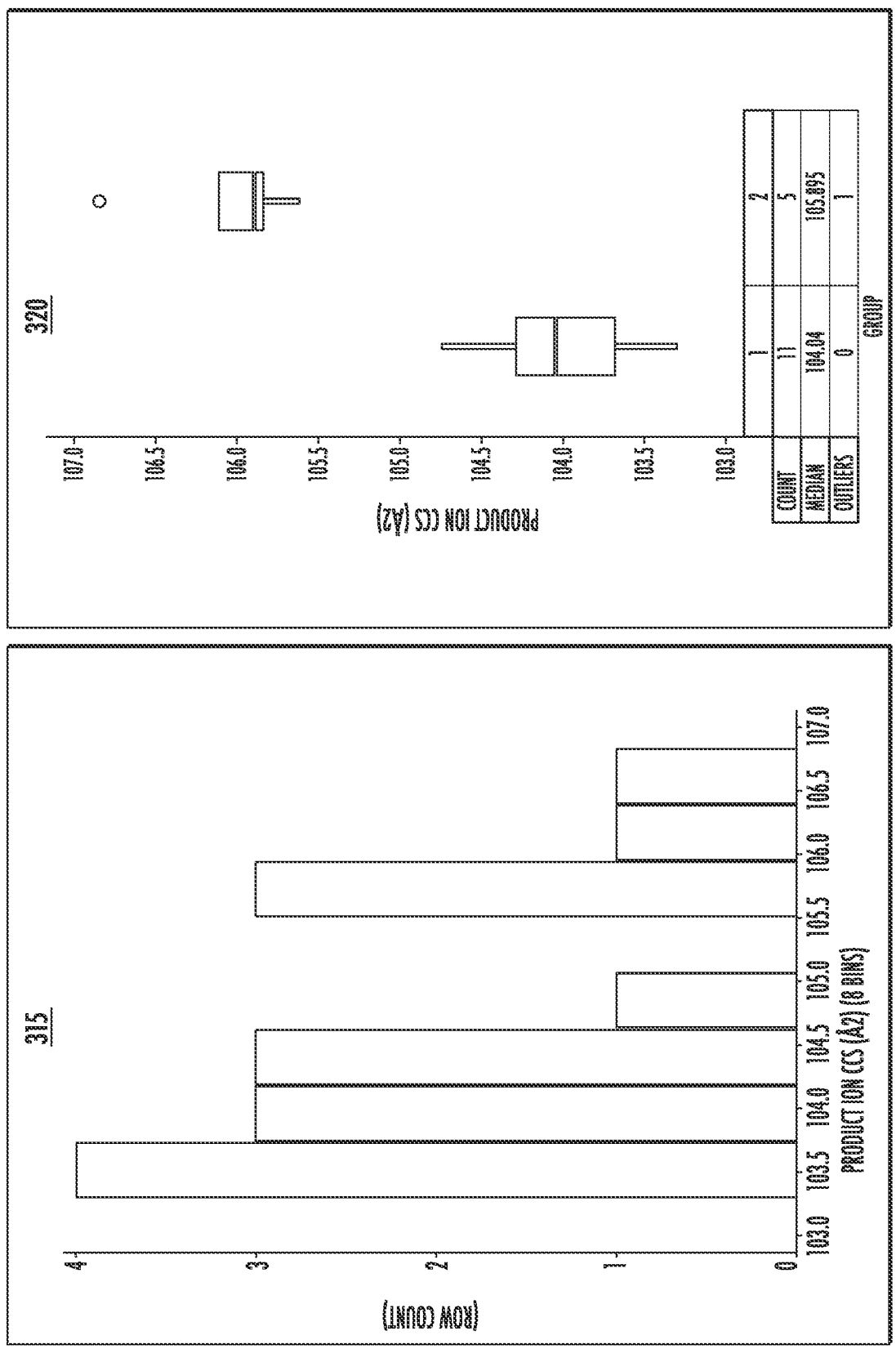
FIG. 3C illustrates CCS information for product ions having the structure $C_6H_{12}N$ (m/z=98.096).

FIGS. 3B-3E depict the results of experiments determining that product ions with the same elemental composition may have different structure and CCS information (i.e., CCS values). The fragmentation for the experiments depicted in FIGS. 3B-3D was conducted within a trap cell (for example, trap cell 230 of FIG. 2). Referring to FIG. 3B, therein is depicted graph 310 illustrating CCS variation for $C_6H_{12}N$ product ions, for example, resulting from fragmentation of the compounds depicted in FIG. 3A. FIG. 3C depicts graphs 315 and 320 generated via analyzing the CCS information associated with FIG. 3B. For example, graph 315 depicts a natural break analysis (for instance, a Jenks natural break optimization) indicating two populations. Referring to graph 320, statistical analysis of these two populations indicates that differentiation may be possible, for example, with a probability (p) of <0.05. The variation within the groups equaled 0.4%, in good agreement with precursor ion CCS measurement precision (for instance, affording comparative analysis and library searching/screening).

Figure 3E:
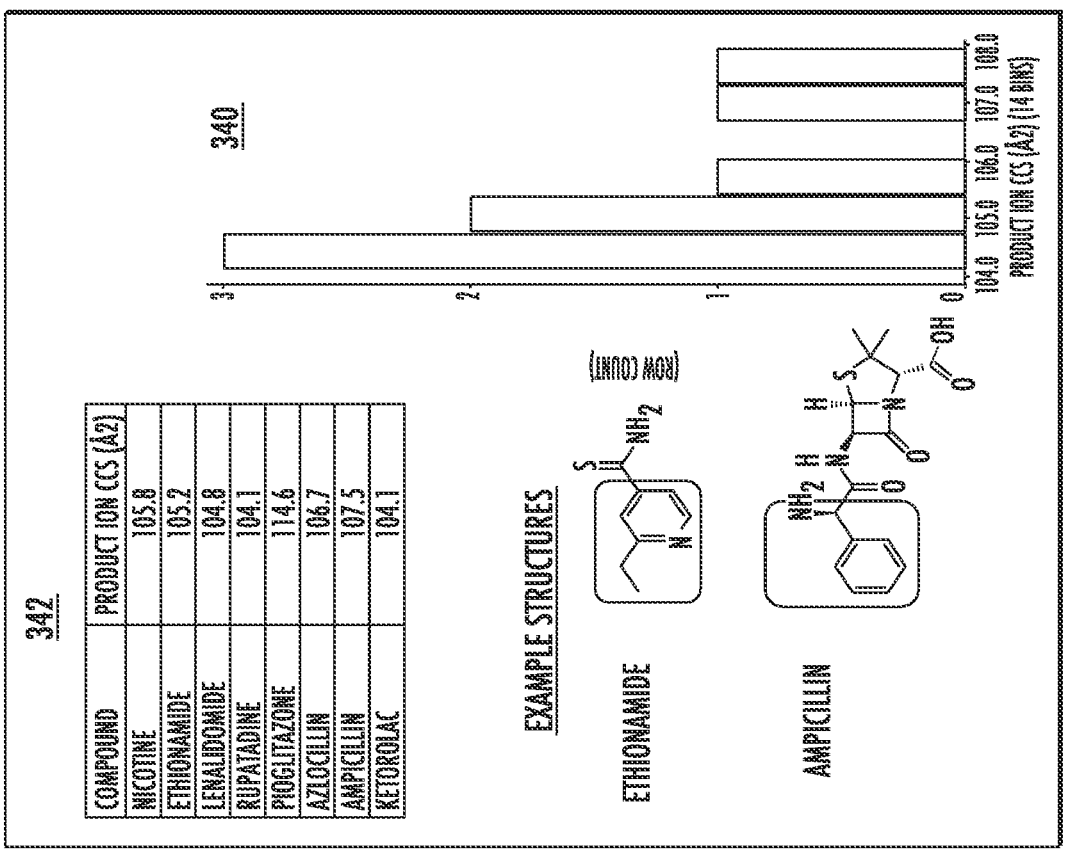
FIG. 3E illustrates CCS information for product ions having the structure $C_7H_8N$ (m/z=105.0335)
Figure 3D:
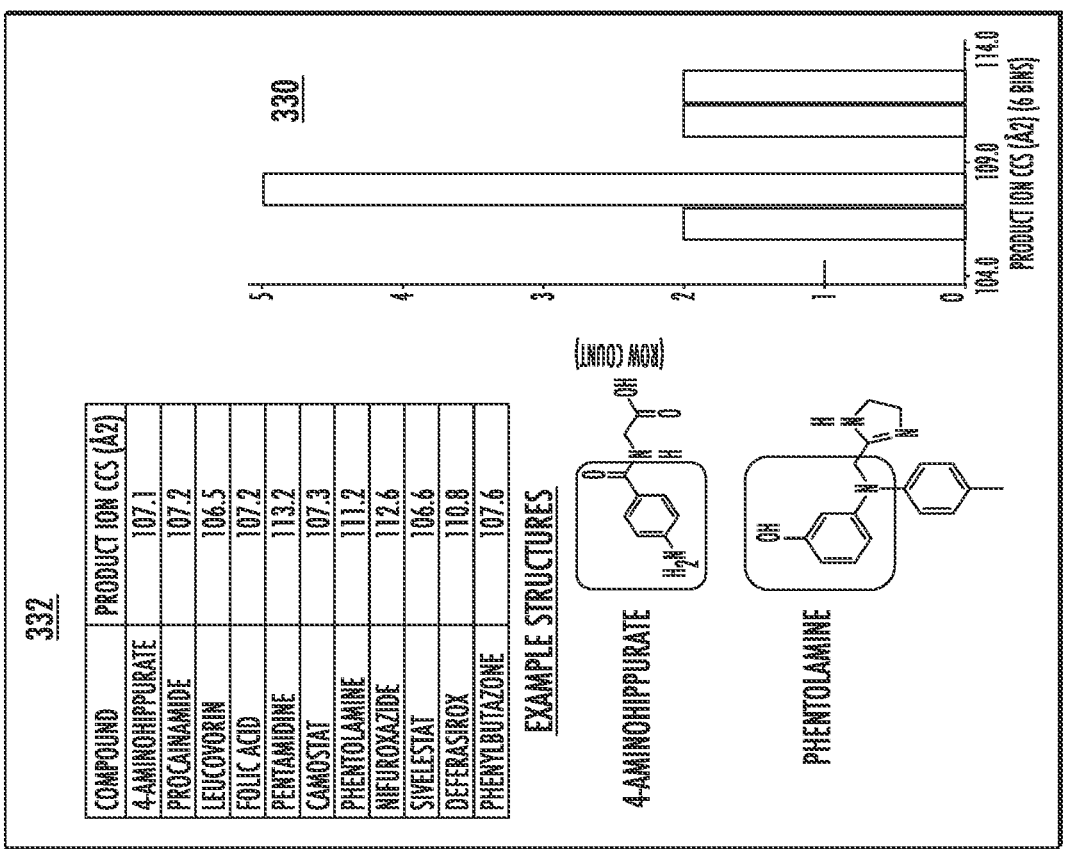
FIG. 3D illustrates CCS information for product ions having the structure $C_7H_6NO$ (m/z=120.0443).

FIG. 3D illustrates graph 330 and CCS information 332 for product ions having the structure $C_7H_6NO$ (m/z=120.0443), and FIG. 3E illustrates graph 340 and CCS information 342 for product ions having the structure $C_7H_8N$ (m/z=105.0335). As depicted in FIGS. 3D and 3E, a natural break may be determined in the CCS information for $C_7H_6NO$ and $C_7H_8N$ product ions.

In some embodiments, CCS variances for various product at different m/z values may be determined. In some embodiments, variances may be determined based CCS values determined for multiple experiments, in comparison to historical information, in silico information, ML/AI, and/or the like. In some embodiments, a variance value may be determined for a particular product ion. In general, a variance may be a percentage, standard deviation, min/max variance threshold of CCS variance. For example, for a product ion, the variance may be 1.13 or 1.13%, while the variance for another product ion may be about 0.36 or 0.36%.

In some embodiments, a variance over a predetermined variance threshold may be used to indicate that the variance is due to structural differences in the product ions (for instance, that the product ions include isomers or other structurally different configurations that effect CCS). Variances below the threshold, for instance, may be statistically insignificant (for instance, due to experimental variances and not due to structural differences). For example, the variance threshold may be 0.5%. Accordingly, a product ion CCS process according to some embodiments may determine that a product ions may have structurally different products (for instance, isomers), while other product ions do not.

In some embodiments, the product ion CCS values for certain product ions may be determined and placed in a product ion CCS library. Accordingly, in some embodiments, when a product ion CCS value (for instance, for a certain product ion structure or m/z value) is obtained, product ion CCS processes according to some embodiments may determine the particular structural form (for instance, isomer) based on the product ion CCS value. For instance, the product ion CCS value for the meta form may be determined to be X, while the product ion CCS value for the ortho form may be Y. Alternatively, in some embodiments, the product ion CCS value may be used to rule out or filter certain product ions and/or structural forms. For instance, the m/z may indicate a product ion having the structure $C_6H_{12}N$, but the product ion CCS value is out of the range for form A, therefore, the product ion $C_6H_{12}N$ being detected may be in form B, form C, etc.

FIGS. 4A-4D depict experimental results of repeat analysis of set of compounds (selected, for example, based on the analysis results depicted in FIGS. 3A-3E). Each of FIGS. 4A-4D depict a graph 405, 415, 425, 435 and associated CCS information showing a repeat analysis (n=6) of a set of compounds that was mixed together based on shared product ion commonality. The results are presented in box and whisker format to demonstrate the variation in product ion CCS measurement. Average/median precision values were 0.1-0.2% but typically <0.5%. Each of FIGS. 4A-D depict in table format (410, 420, 430, 440) the observations (left table), and the average, median, standard deviation and CV values (right table). Outliers, in terms of CV are typically caused by measurements associated with poor ion statistics and were not removed from the analysis. In tables 410, 420, 430, and 440 of FIGS. 4A-D, the bottom left table show example comparative analysis (p-value from a standard Student's T-test) for a binary comparison where differentiation was possible or not based on the observed product ion CCS values. In some examples, the number of detections can be greater than the number of injections which may be a result, of, for example, multiple detection of the same target analyte across the same chromatographic peak, typically so-called 'shoulders', which were treated as independent observations.

Figure 4B:
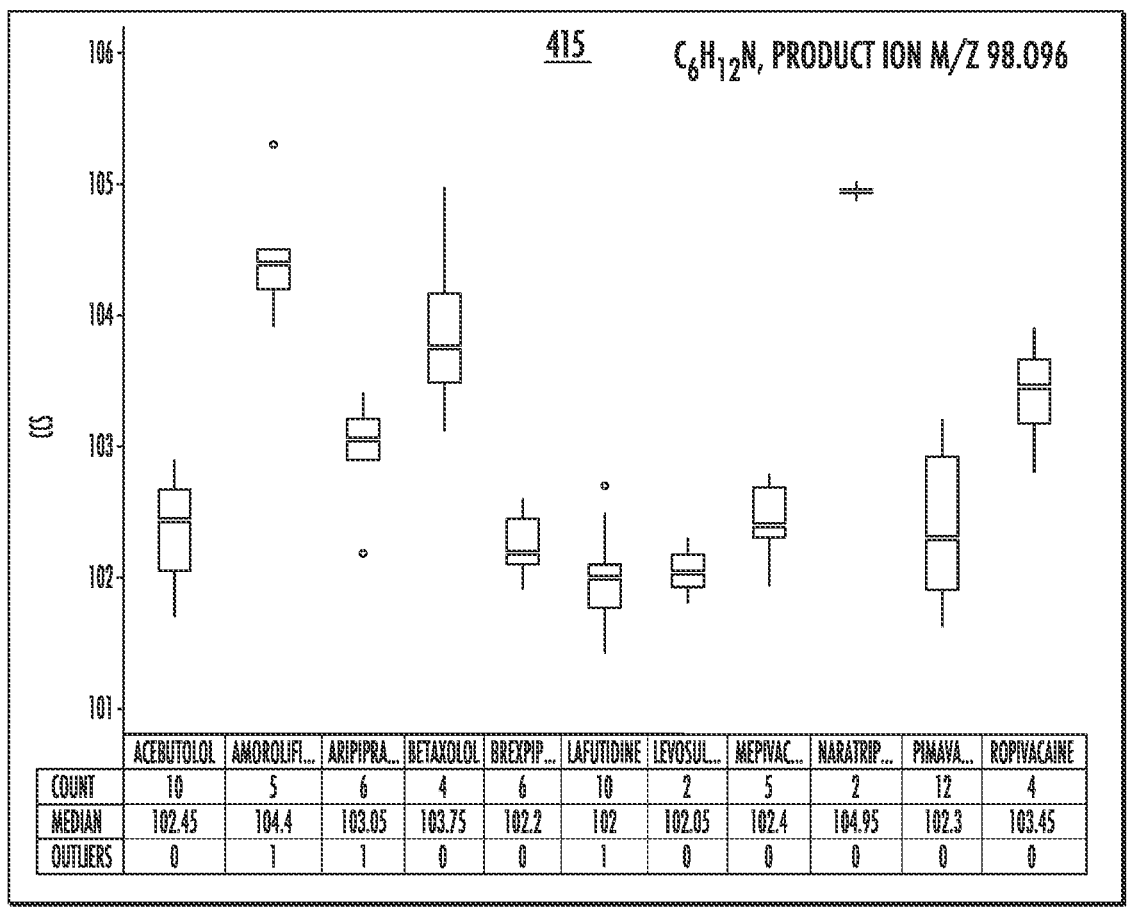
FIG. 4B illustrates a graph of CCS versus m/z for product ions having the structure $C_6H_{12}N$ (m/z=98.096) according to some embodiments.
Figure 4C:
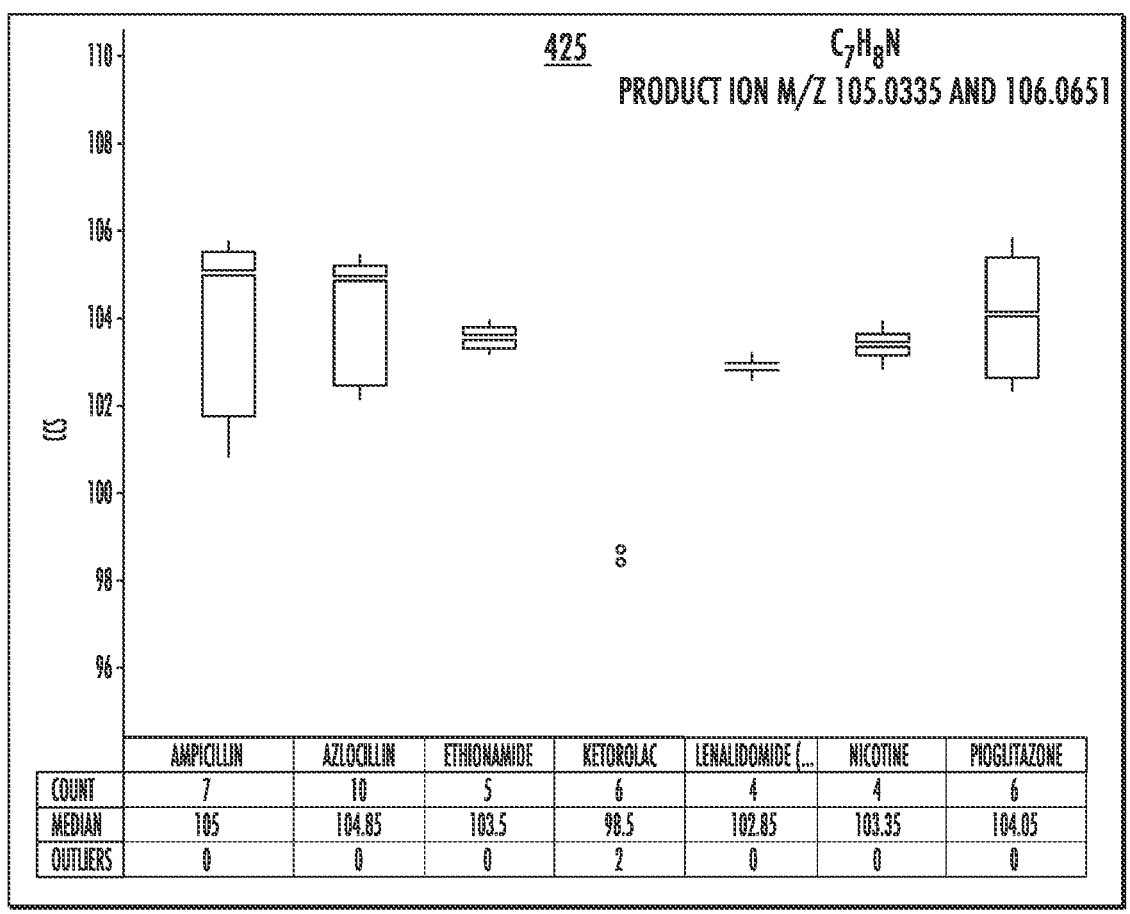
FIG. 4C illustrates a graph of CCS versus m/z for product ions having the structure $C_7H_8N$ (m/z=105.0335 and 106.0651) according to some embodiments.
Figure 4D:
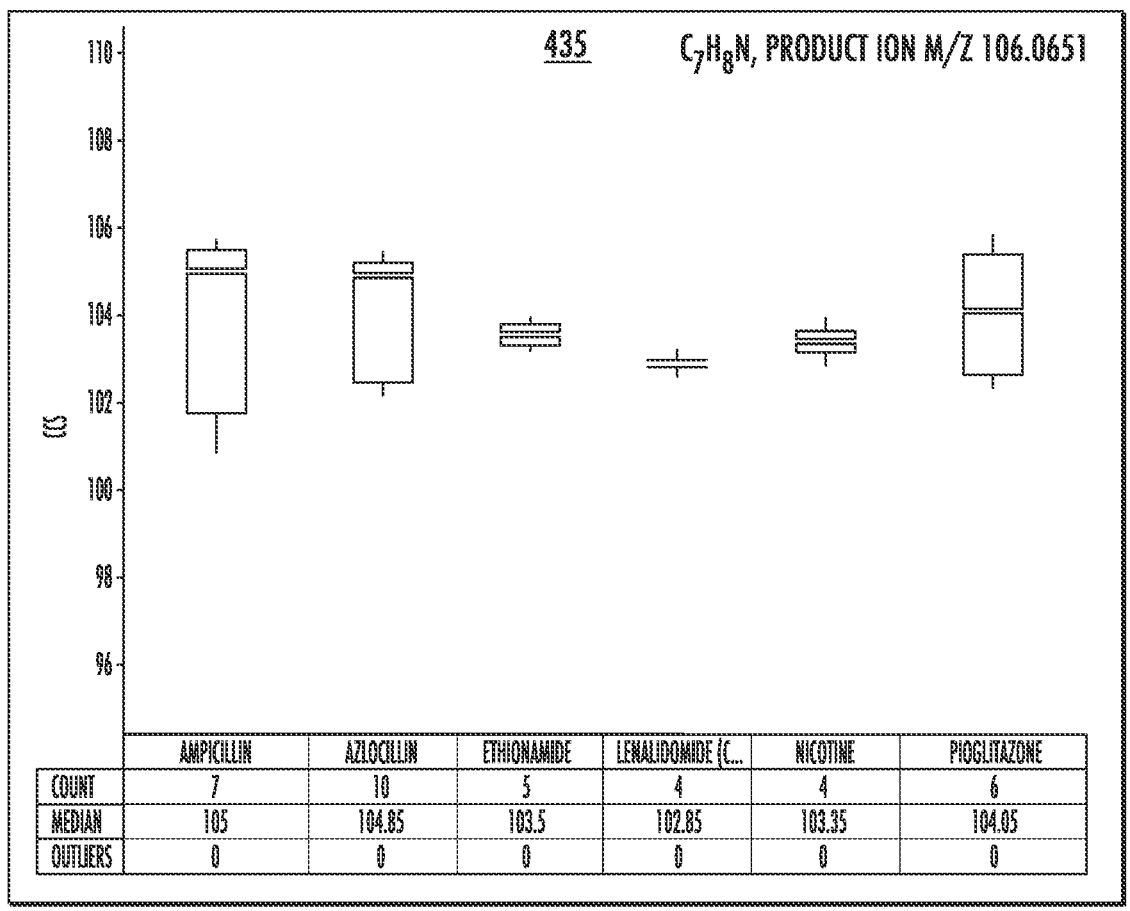
FIG. 4D illustrates a graph of CCS versus m/z for product ions having the structure $C_7H_8N$ (m/z=106.0651) according to some embodiments.
Figure 5A:
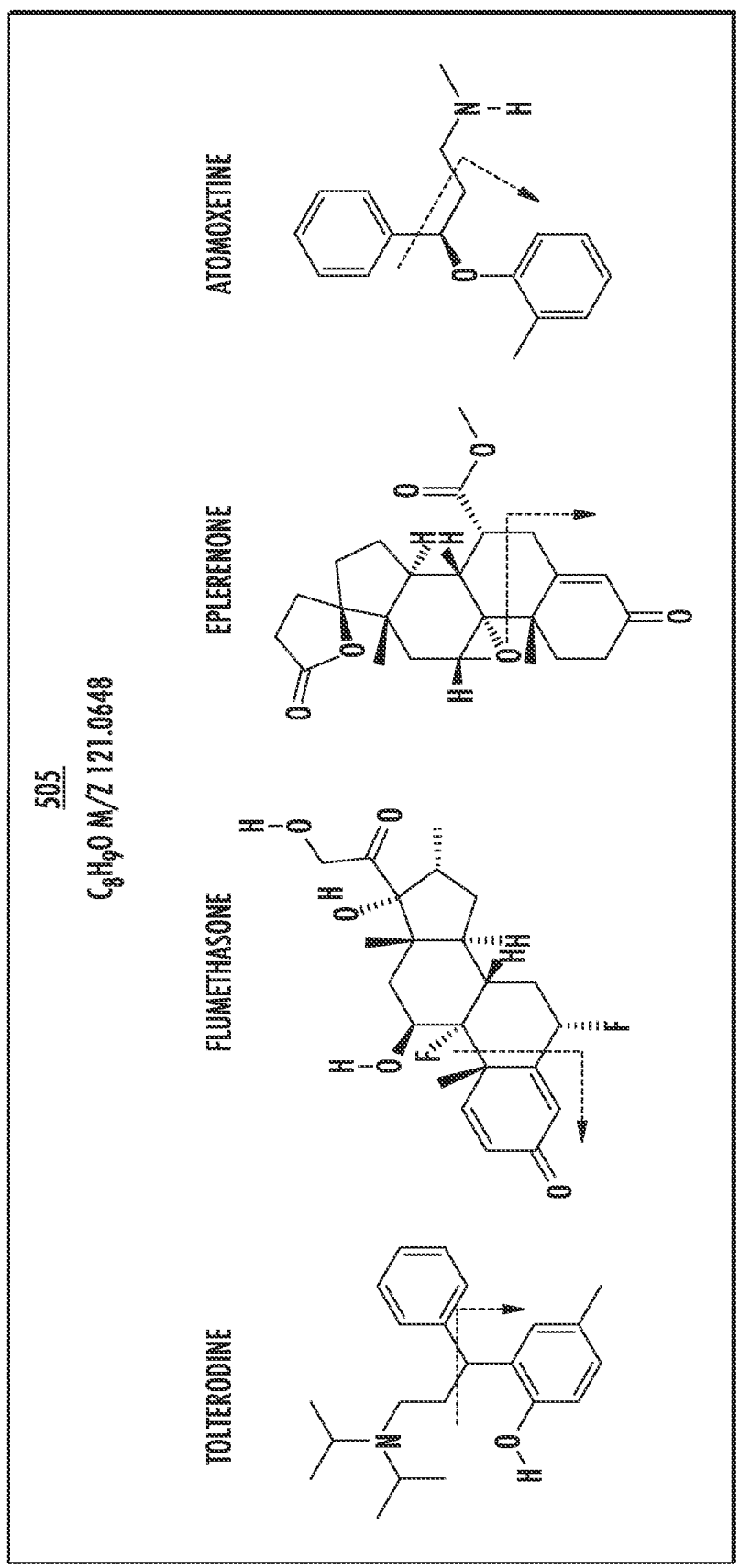
FIG. 5A illustrates precursor ions that may generate product ions having the structure $C_8H_9O$.
Figure 5B:
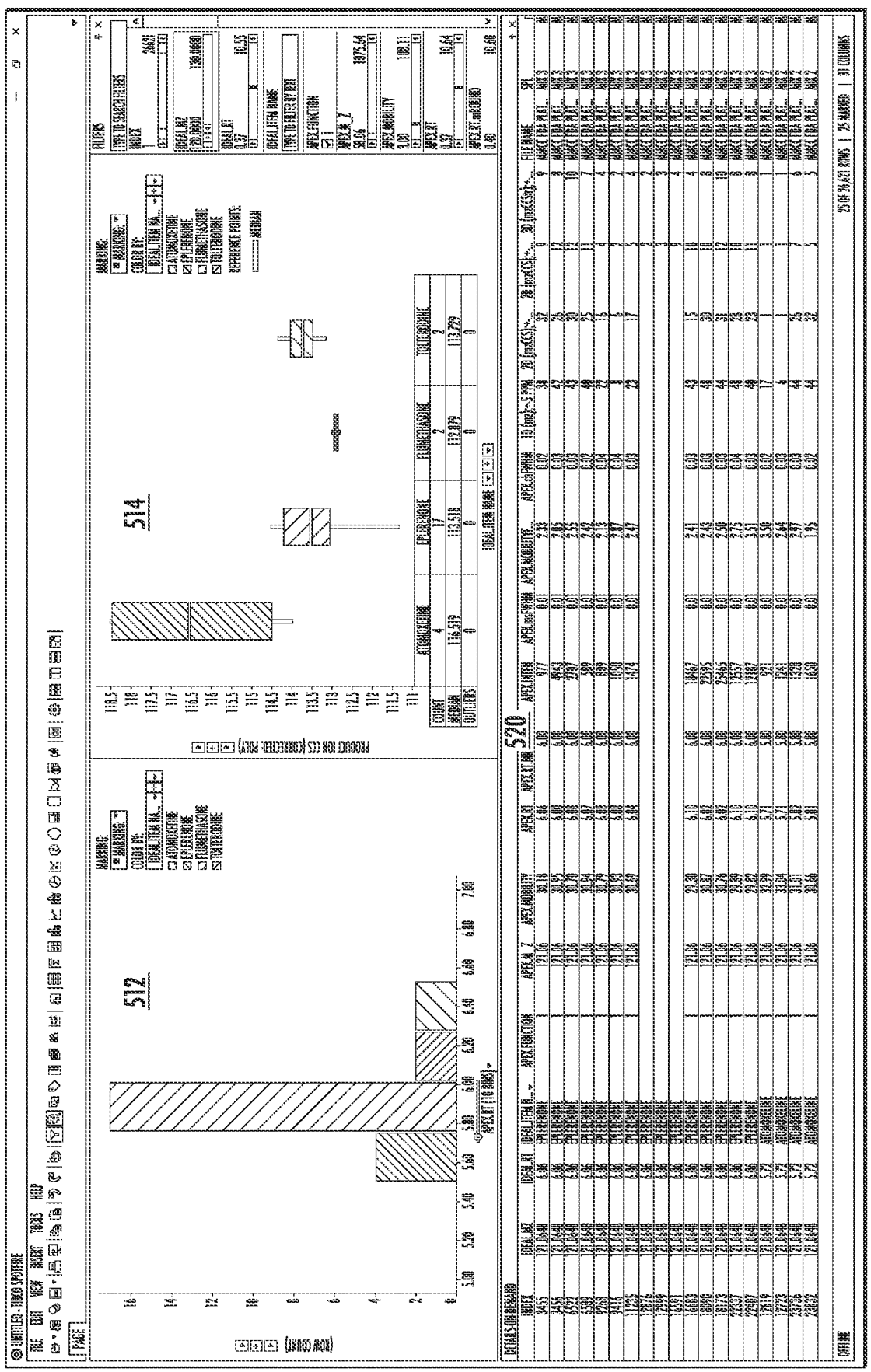
FIGS. 5B-D illustrates analytical information for co-eluting product ions having the structure $C_8H_9O$ according to some embodiments.
Figure 5C:
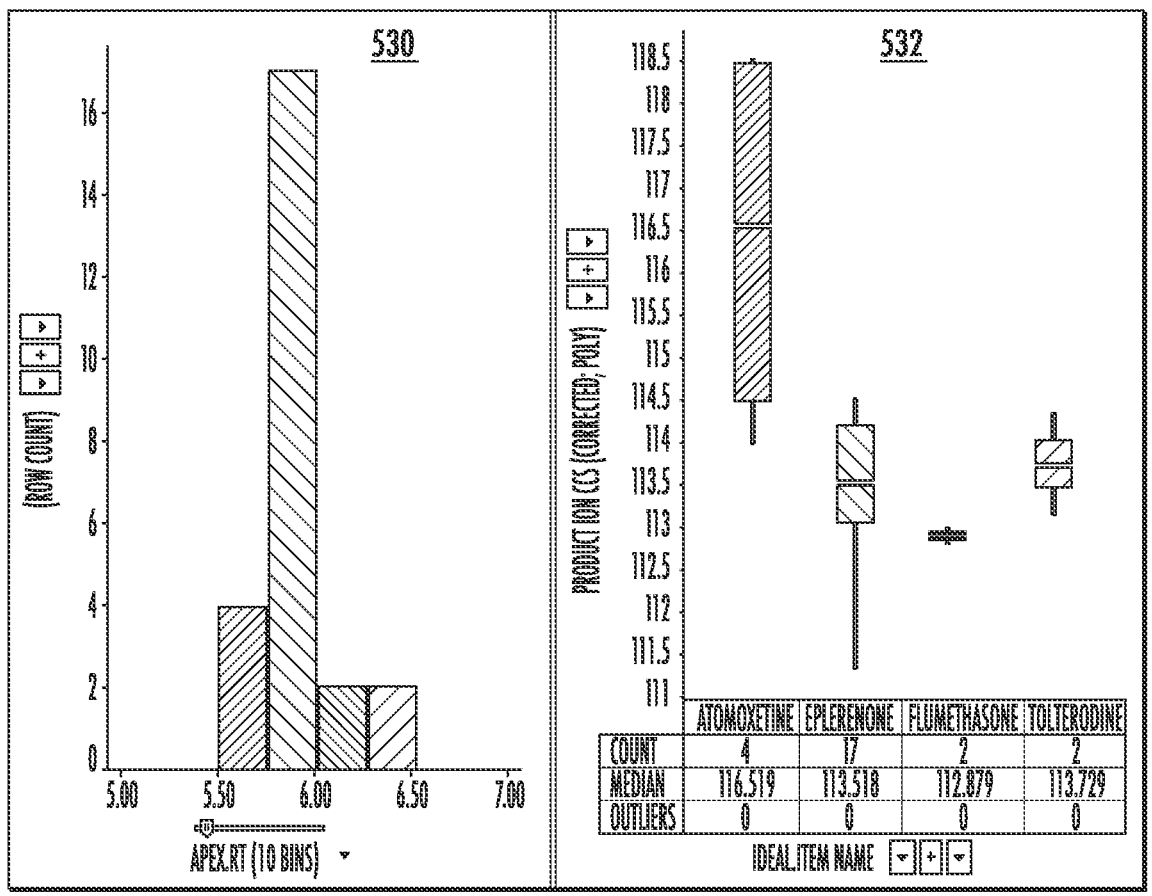
Figure 5D:
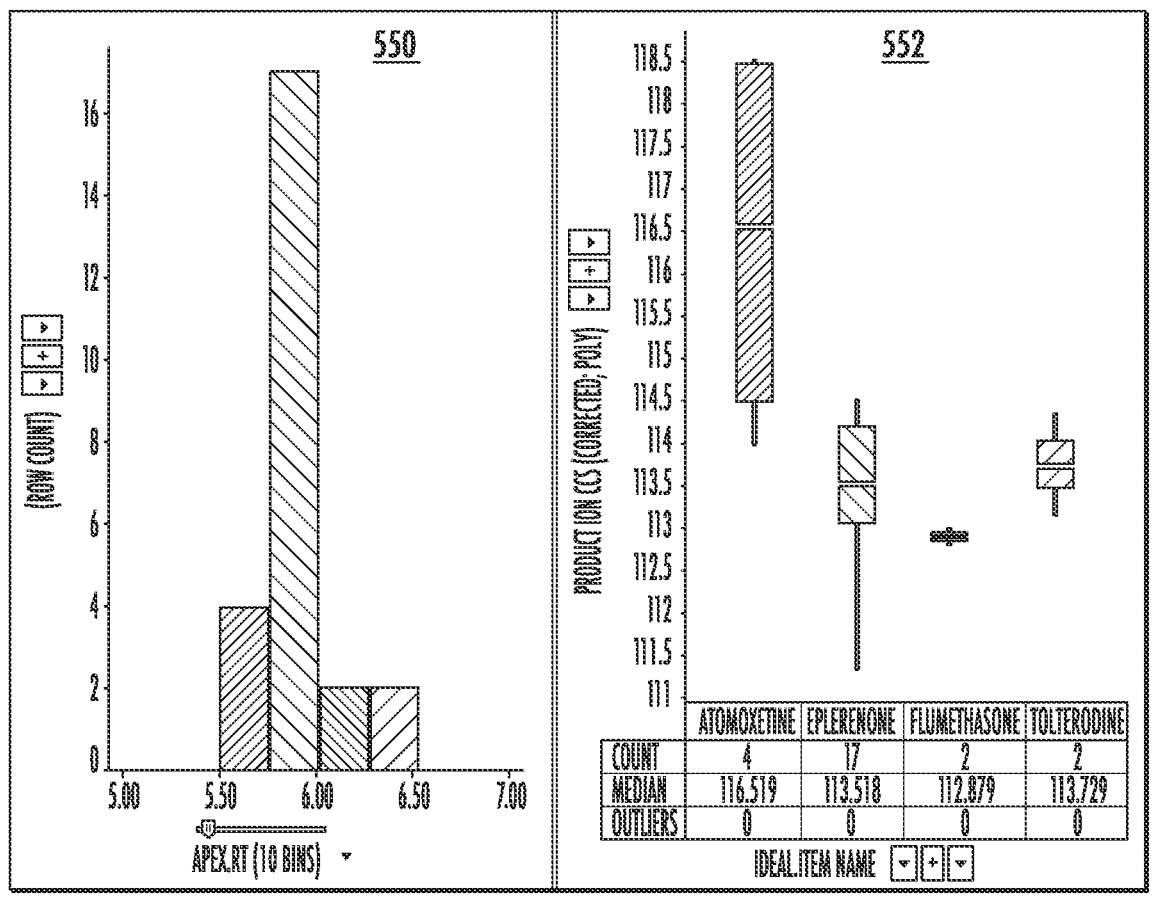

FIG. 4A illustrates a graph 405 of CCS versus m/z for product ions having the structure $C_7H_6NO$ (m/z=120.0443) and corresponding information table 410 according to some embodiments. FIG. 4B illustrates a graph 415 of CCS versus m/z for product ions having the structure $C_6H_{12}N$ (m/z=98.096) and corresponding information table 420 according to some embodiments. FIG. 4C illustrates a graph 425 of CCS versus m/z for product ions having the structure $C_7H_8N$ (m/z=105.0335 and 106.0651) and corresponding information table 430 according to some embodiments. FIG. 4D illustrates a graph 435 of CCS versus m/z for product ions having the structure $C_7H_8N$ (m/z=106.0651) and corresponding information table 440 according to some embodiments FIGS. 5A-5D illustrate the inclusion of LC separation in the analysis according to some embodiments. For instance, FIGS. 5B-5D depict analysis results with a set of (near) co-eluting components selected from structures and common fragment ion in terms of elemental composition of the compounds 505 depicted in FIG. 5A (i.e., product ions having the structure $C_8H_9O$ (m/z=121.0648)). FIG. 5B illustrates graphs 512 and 514 and corresponding analytical information 520 for co-eluting product ions having m/z=121.0648 according to some embodiments. For instance, FIG. 5B depicts an overall summary of the targeted analysis of the analysis of repeat experiment with the reconstructed chromatogram 512 and the product ion CCS value distribution 514, along with data table 520. For example, box-and-whisker plots—514 suggest the present of 2 or 3 distinct product ion CCS distributions. FIG. 5C depicts graphs 530 and 532 illustrating that two early eluting compounds are selected and the summary tables 540 the average/median retention time and % CV values. Here, differentiation was feasible based on product ion CCS. In FIG. 5D, similar results for the two later eluting compounds are depicted in graphs 550 and 552, along with summary table 560. Here, separation based on typically intra-experiments CV values would not possible; however, statistical analysis of the box-and-whisker plot results (550, 552) indicates that separation could be feasible.

In some embodiments, various different types of analytical information may be used to analyze sample components. The previous results were obtained with fragmentation conducted in the trap region of an analytical system (for instance, trap cell 230 of system 260), providing MS/MS data that can be annotated with product ion CCS values, for example, as shown FIG. 6. However, the geometry of an instrument (for example, system 260) may afford fragmentation in both the trap (for instance, 230 of FIG. 2) and transfer (for instance, 236 of FIG. 2) regions of the instrument of which the experiment (see, for example, FIG. 8), providing precursor and product ion CCS data in a single experiment (see, for example, FIGS. 9-11).

Figure 6:
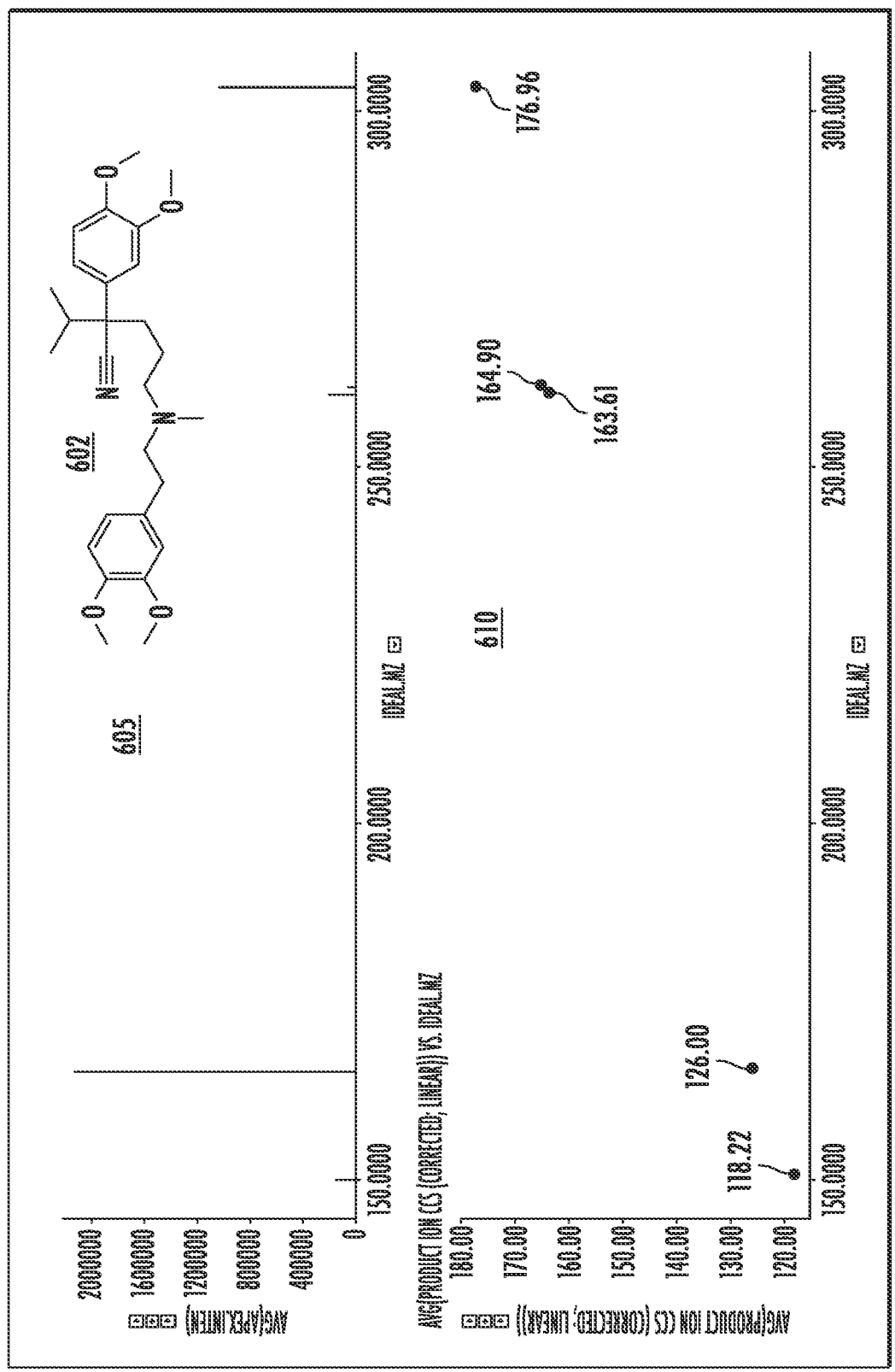
FIG. 6 illustrates embodiments of two-dimensional (2D) product ion spectra.

For example, FIG. 6 illustrates embodiments of product ion spectra for experiments according to some embodiments. As shown in FIG. 6, a graph 605 of peak apex vs. m/z for compound 602 may be generated, for instance, via analysis systems 160 or 205. In another example, graph 610 of product ion CCS vs. m/z may be generated for compound 602. Analytical information, such as the information depicted in graphs 605 and/or 610 may be used to generate 2D CCS fingerprints for compounds, such as product ions fragmented according to some embodiments. In other embodiments, analytical information, such as CCS, m/z, and intensity information, may be used to determine 3D fingerprints for compounds. In various embodiments, product ion spectra according to some embodiments may be used, among other things, to improve the specificity of mass analysis experiments as compared with conventional methods. Embodiments are not limited in this context.

Figure 7:
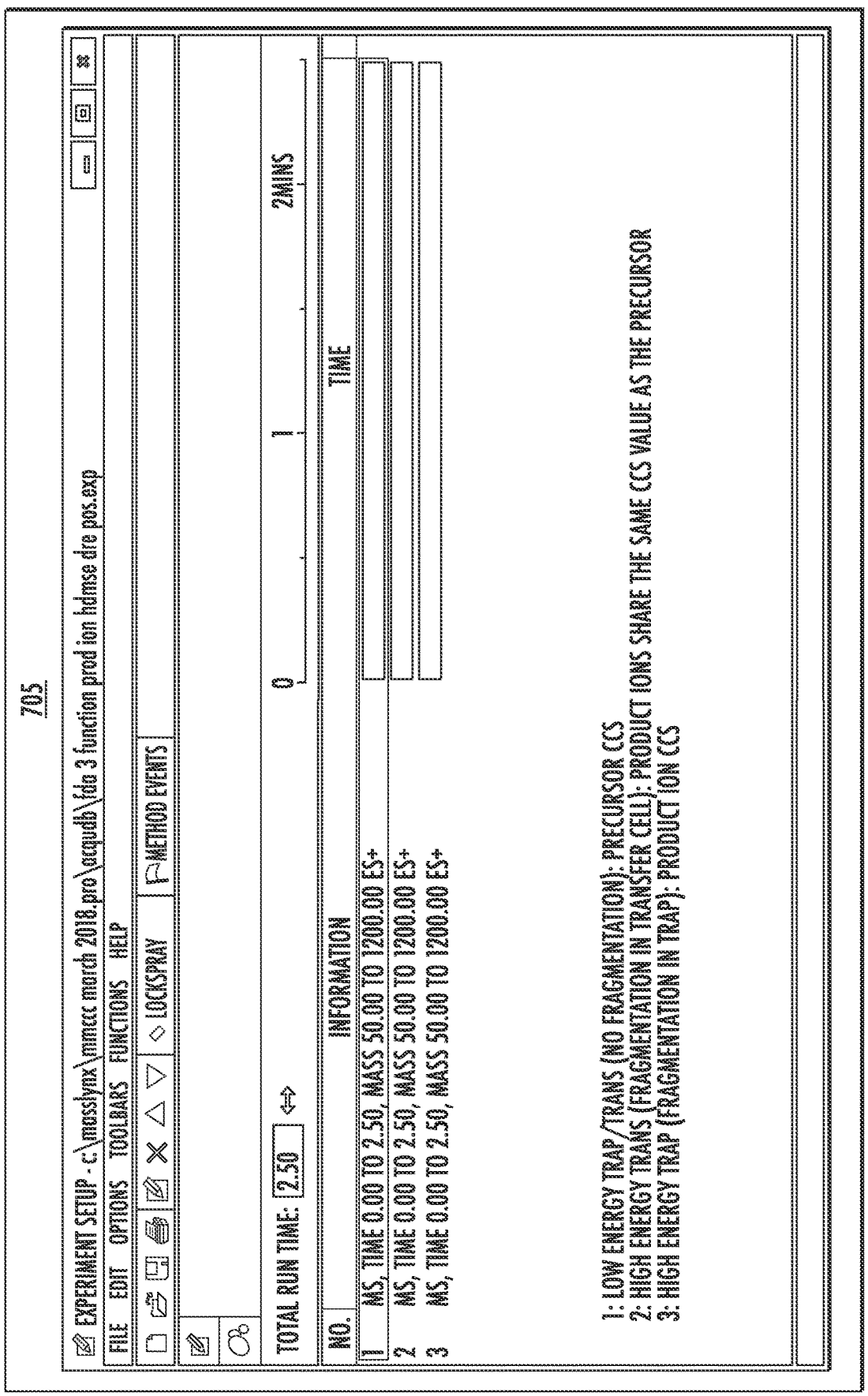
FIG. 7 illustrates a three-function experiment design according to some embodiments.

FIG. 7 illustrates a three-function experiment design according to some embodiments. In some embodiments, product ion CCS processes may use a three-function or three-channel TAP fragmentation process. For example, as shown in FIG. 7, the following three-channel experiment may be performed: Function 1: conventional low energy trace (for example, low energy trap/transfer (no fragmentation); Function 2: HDMSe-like high energy trace with transfer fragmentation (for example, high energy transfer (fragmentation in 236); product ions share the same CCS value as the precursor); Function 3: high energy trace with trap fragmentation (for example, High energy trap (fragmentation in trap cell 230); product ion CCS). Product ion CCS processes may operate to cross-correlate the three-channel information according to the following: channels 1 and 2 to obtain product ions based on shared drift time; and cross-correlate between channels 2 and 3 to derive CCS values for product ions.

Figure 8:
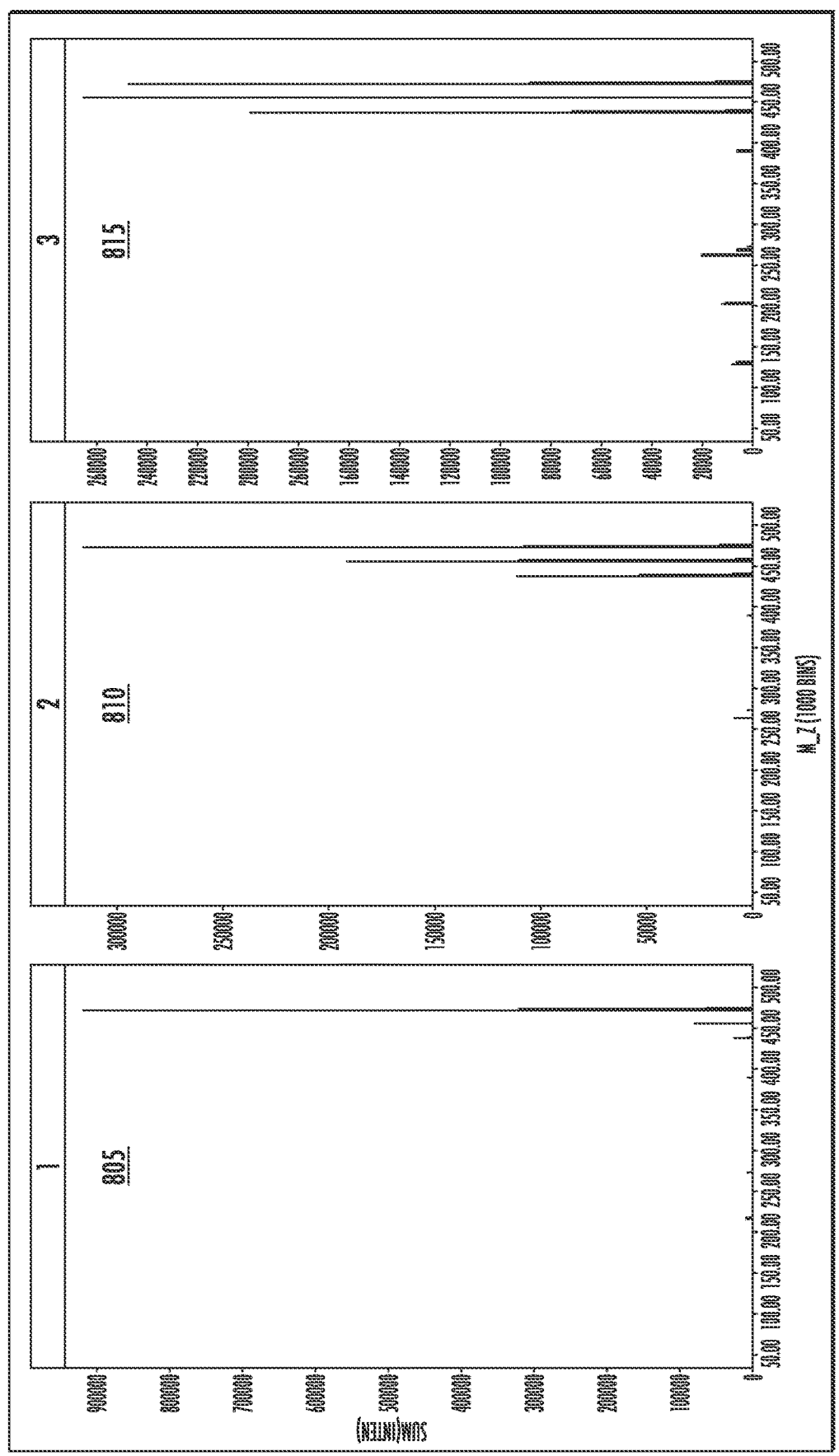
FIG. 8 illustrates MS and MS/MS results information for a three-function experiment according to some embodiments.
Figure 9:
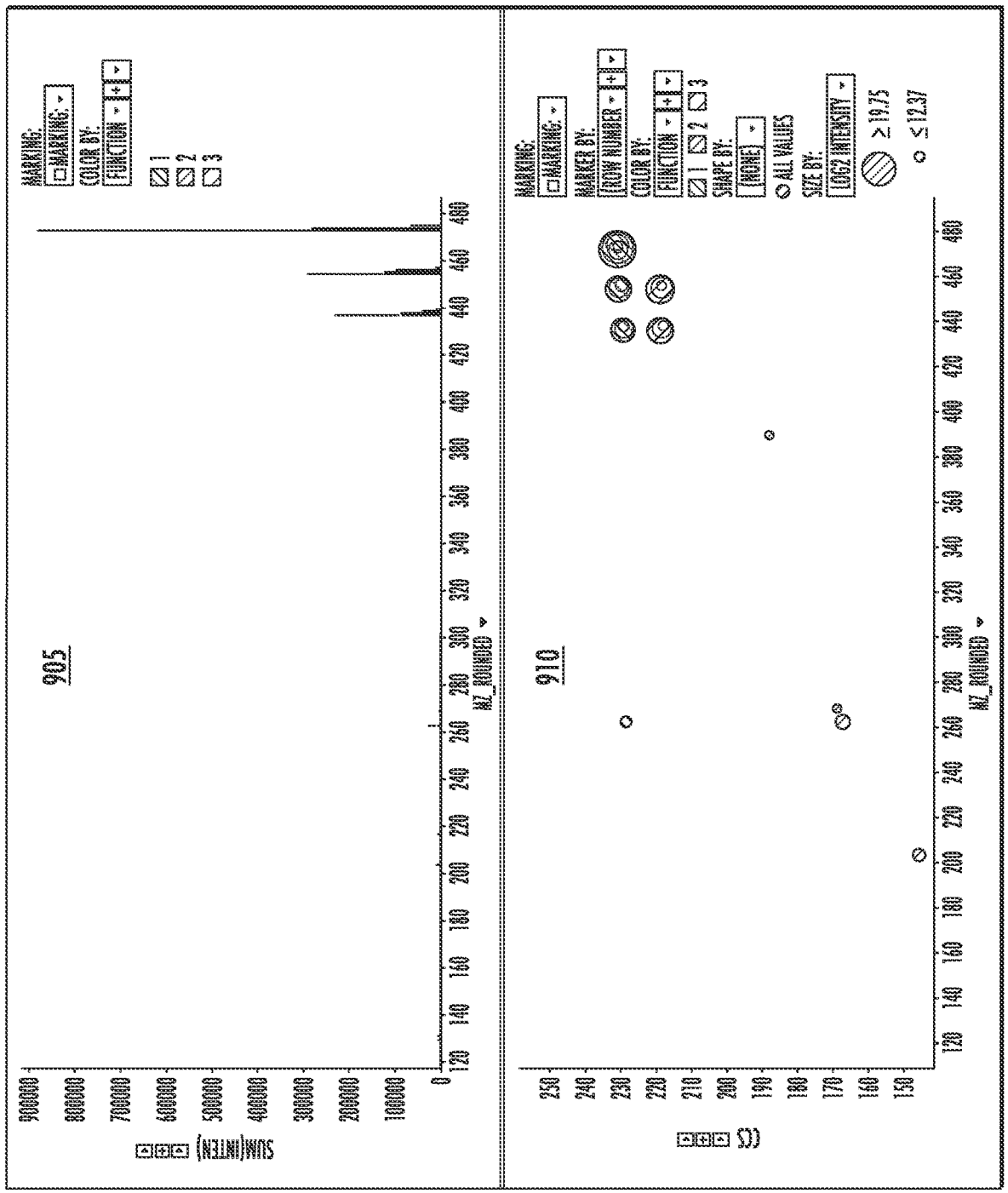
FIG. 9 depicts a 2D IMS precursor/product ion CCS profile map for Terfenadine according to some embodiments.
Figure 11:
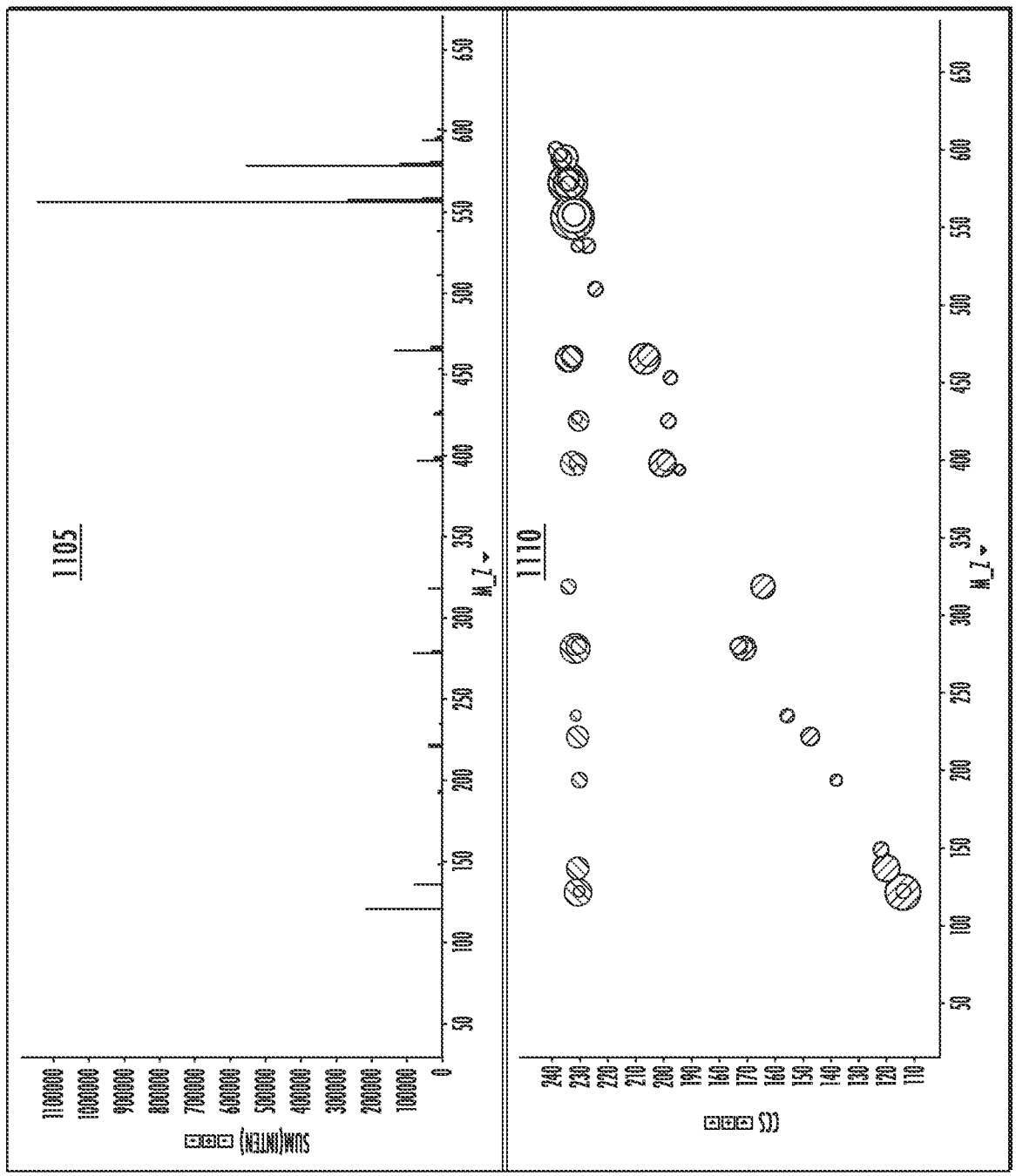
FIG. 11 depicts a 2D IMS precursor/product ion CCS profile map for leucine enkephalin (LeuEnk) according to some embodiments.

FIG. 8 shows that three-function experiment data according to some embodiments may be processed with development software (for instance, ApexRT), providing MS and MS/MS spectra that can be annotated with CCS information. More specifically, graph 805 depicts results for function 1 (LE precursor CCS), graph 810 depicts results for function 2 (TAP transfer HE), and graph 815 depicts results for function 3 (TAP trap HE product ion CCS). Example annotations are shown in FIGS. 9 and 11, which are derived from the LC-MS analysis of a standard mixture showing the combined/summed MS and MS/MS data/spectra at the top (905 and 1005) and a 2D precursor/product ion CCS map at the bottom (910 and 1010).

FIG. 10 depicts empirical and predicted CCS information for Terfenadine according to some embodiments. In some embodiments, the predicted product ion CCS values of FIG. 10 were determined using ML/AI according to some embodiments. The predicted product ion CCS values may have various uses and provide multiple technological advantages over conventional techniques. One non-limiting technological advantages is that the predicted product ion CCS values may facilitate the development of 2D CCS maps (for instance, FIGS. 9 and 11) in the absence of empirical data.

In some embodiments, profiling of known-unknowns may be determined using Liquid Chromatography-Ion Mobility-Mass Spectrometry (LC/IM/MS). In the following case study, LC/IM/MS has been used to profile the unknowns of *Passiflora* complement. However, embodiments are not limited in this regard, as the described processes may be applied to various other compounds.

C-Glycosyl flavonoids can be used as markers in the quality control of *Passiflora* phytomedicines. Several studies have focused on fingerprint analysis, quantification or identification of flavonoids in *Passiflora* using LC-MS and the principles of utilizing the combined specificity of LC-IM-MS for "known-unknown" isomer profiling of *Passiflora* species demonstrated. However, structural elucidation of identified flavonoids responsible for contribution to phytochemical activity is still required. Hence, the application of LC-MS methods to profile flavonoid markers has significantly increased. Here, the analysis of *Passiflora* extracts been performed to generate "known-unknown" speciation profiles. This approach can be combined with historical profiling of product ion identifications. Moreover, experimentally attained information was combined with CCS prediction to perform retention time independent elucidation of known flavonoids. More detailed application background information has been provided in McCullagh et al., "Use of ion mobility mass spectrometry to enhance cumulative analytical specificity and separation to profile 6-C/8-C-glycosylflavone critical isomer pairs and known-unknowns in medicinal plants," Phytochem Anal. 2019 July; 30(4):424-436 ("McCullagh") and Pereira et al., "Distinction of the C-glycosylflavone isomer pairs orientin/isoorientin and vitexin/isovitexin using HPLC-MS exact mass measurement and in-source CID," Phytochem Anal. 2005 September-October; 16(5):295-301 ("Pereira").

EXPERIMENTAL

Samples were prepared and LC-IM-MS data collected as previously described in McCullagh and Pereira. Briefly, voucher specimens of *Passiflora incarnata, edulis, caerulea* and *alata*, were employed in this study. Briefly, the materials were dried at 35° C. for 48 hours, powdered and ground. Leaf material was mixed with ethanol:water and the flavonoids extracted by SPE. LC separation of the filtered and diluted extracts was performed with an UPLC system operated under standard reversed-phase chromatographic conditions. IM-MS data were collected on an ion mobility-enabled hybrid orthogonal acceleration quadrupole time-of flight (Q-IM-oaTof) mass spectrometer. Development software was used to peak detect and lock mass correct the LC-IM-MS data in multiple dimensions. Following alignment and co-detection, matrix characterized libraries were created and re-imported into the analysis software. $^{TW}CCS_{N2}$ predictions were conducted with an in-house developed model. More details are provided in: McCullagh and Pereira.

Informatics. A custom version of UNIFI Scientific Information System (Waters Corporation) was used to peak detect and lock mass correct the LC-IM-MS data in multiple dimensions ($t_r$, $t_d$, m/z, and intensity). Default processing parameters were used and the data sets exported in native UNIFI format. Next, the data were further analyzed in Progenesis QI (Nonlinear Dynamics, Newcastle upon Tyne, UK), employing alignment and co-detection across samples, using default processing parameters, detection threshold excepted, to match UNIFI peak detections, which was set to a floor level of zero, providing data matrices to construct "known-unknown" libraries. The latter was achieved by exporting the peak detected data as fragment databases and so-called additional property tables, comprising retention time and $^{TW}CCS_{N2}$ values, in msp and csv format, respectively. The resulting msp and csv tables were converted and merged to worksheets using development software[21] and imported into the Scientific Library of UNIFI Scientific Information System. Only features with product ions that were detected in two out of three technical replicates were retained in variant specific libraries.

Machine Learning Procedure. $^{TW}CCS_{N2}$ predictions were obtained with a model trained with machine learning. The approach is similar to the method of Zhou et al., "Large-scale prediction of collision cross-section values for metabolites in ion mobility-mass spectrometry," *Anal. Chem.* (2016), but is trained with $^{TW}CCS_{N2}$ to fit an appropriate model. The $^{TW}CCS_{N2}$ data that were internally acquired with IMS-Q-oaToF and Q-IMS-oaToF geometries and covers a wide range of polarity and a large number of chemical classes. For each compound, 196 chemical descriptors were extracted (see, for example, Bouwmeester et al., "Comprehensive and Empirical Evaluation of Machine Learning Algorithms for Small Molecule LC Retention Time Prediction," Anal. Chem. (2019), and Landrum, G., "The RDKit Documentation—The RDKit 2016.09.1 documentation," (2016)) and a model was trained with a gradient boosting algorithm (see, for example, Chen, T. & Guestrin, C., "XGBoost," *Proceedings of the 22nd ACM SIGKDD International Conference on Knowledge Discovery and Data Mining—KDD '16* (2016)). $^{TW}CCS_{N2}$ predictions for compounds described here were obtained using a nested 10-fold cross-validation strategy (see, for example, Bouwmeester et al. and Wessels, L. F. A. et al., "A protocol for building and evaluating predictors of disease state based on microarray data," *Bioinformatics* (2005). This means that the compounds and their $^{TW}CCS_{N2}$ predictions were not part of the training set used for optimizing the model parameters and hyperparameters.

Figure 12:
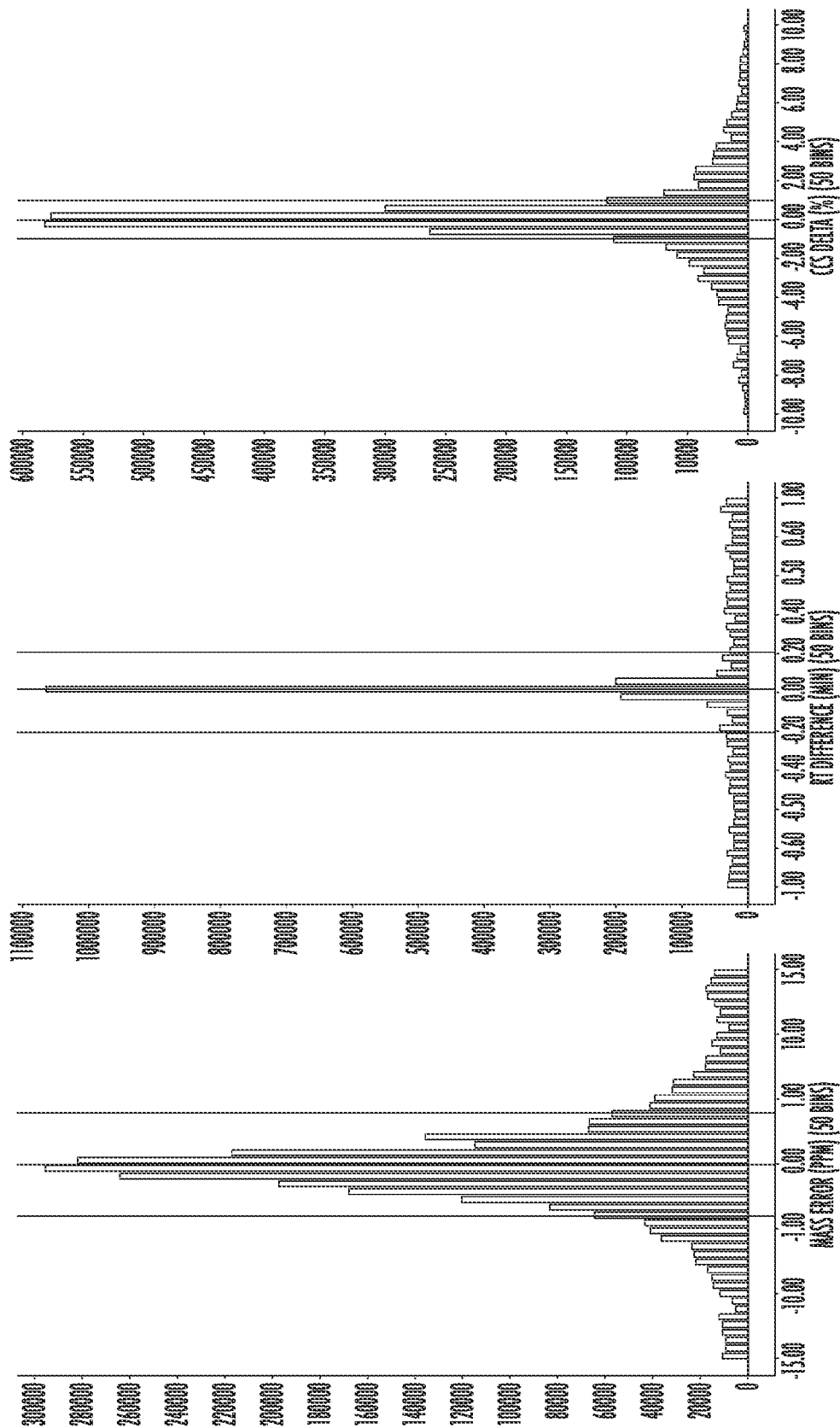
FIGS. 12-19 depict various aspects of profiling of known-unknowns determined using Liquid Chromatography-Ion Mobility-Mass Spectrometry (LC-IM-MS) according to some embodiments.

Results and Discussion:

Known-unknowns. "known-unknown" libraries were constructed as described in the section Experimental, above. Query tolerances for $t_r$, $t_d$ and m/z were determined by creating subset libraries of n−1 (variant of interest excluded) data sets for the individual *Passiflora* variants and the remaining data set used to determine suitable tolerance settings. A single standard deviation of the search result error for all dimensions was used as a measure for the search tolerances, which equaled 0.2 min, 1% and 4 ppm for the $t_r$, $t_d$ and m/z dimensions, respectively, which is in good agreement with the tolerances typically used for library-based screening applications (see, for example, Bauer et al., "Evaluation and validation of an ion mobility quadrupole time-of-flight mass spectrometry pesticide screening approach," *J. Sep. Sci.* (2018)). An example of non-filtered, wide search tolerance m/z, $t_r$, and $t_d$ distributions are shown in FIG. 12, demonstrating the empirically derived tolerance/error widths for "known-unknown" queries as dashed lines. using tolerances of 1 min, 10% and 10 ppm, increased the number of detected features by only 27.6%, suggesting high specificity afforded by combining three query dimensions.

Figure 13:
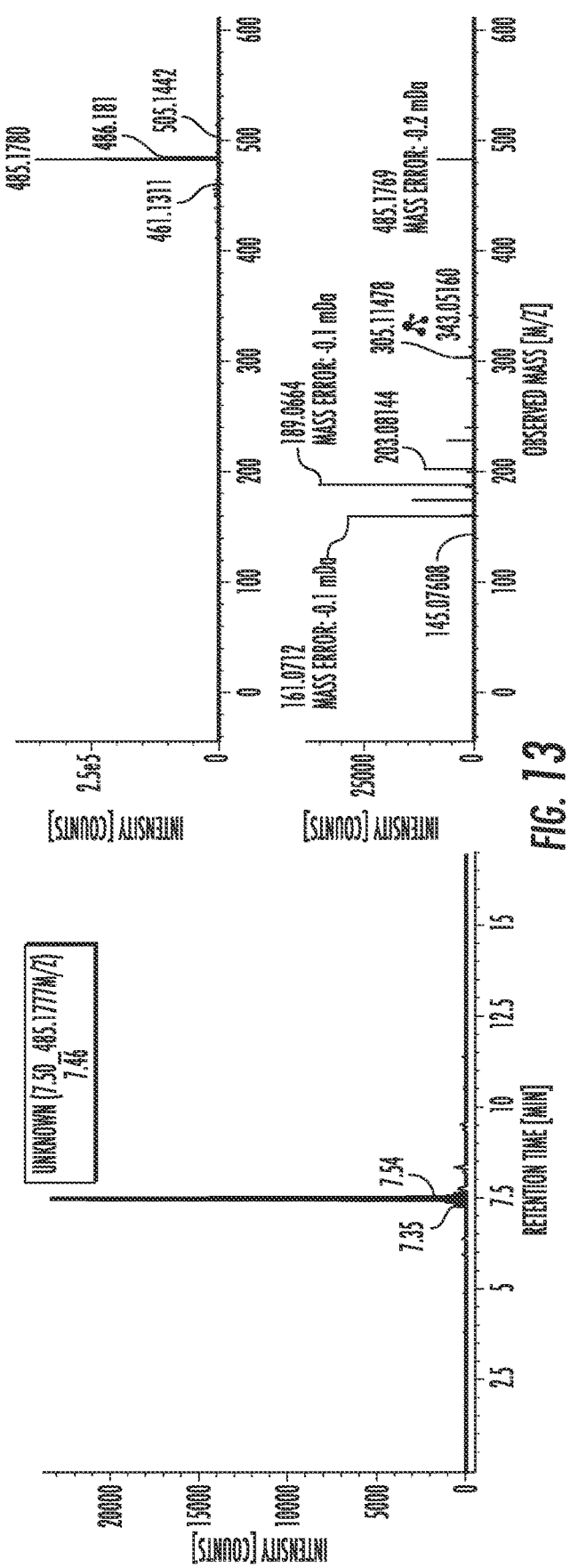
Figure 14:
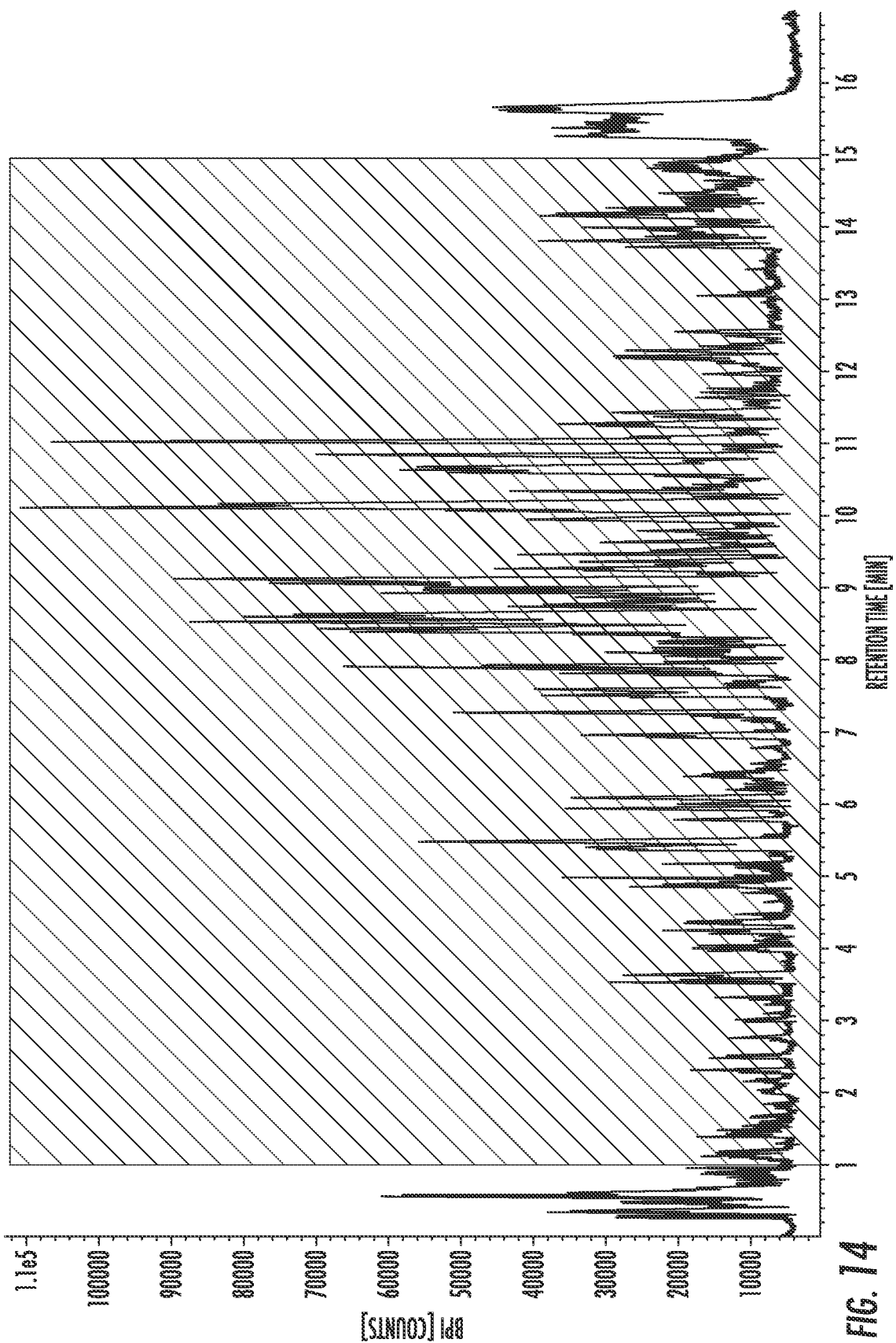

The results shown in FIG. 13 illustrate an example "known-unknown" identification based on searching *P. edulis* against a known unknown *P. alata* library using the afore mentioned tolerances of 0.2 min, 1% and 4 ppm. To investigate how many variant unique features could be detected, queries were conducted, as a single search, with the data from one variant against the libraries of the three other *Passiflora* variants of interest. The chromatographic search space was further reduced to an analyte elution window from 1 to 15 min, as shown in FIG. 14, to exclude injection void and gradient flush detections from the analyses of the data. In addition, a variant specific abundance threshold was applied, which was derived from the analyses of the data of technical replicates.

The results of the profiling experiments are summarized in the following Table 1:

TABLE 1

Table 2. Detection and screening results overview for the investigated *Passiflora* variants with retention time (feature/'known-unknown' compound detected between 1 and 15 min) and area peak detection restrictions (threshold = lowest abundant detected feature/variant).

|  | *Passiflora* variant | | | |
| --- | --- | --- | --- | --- |
|  | edulis | alata | caerulea | incarnata |
| # features detected in 2/3 replicates | 1246 | 1604 | 1510 | 1509 |
| # features detected in 3/3 replicates | 7104 | 6868 | 7102 | 6464 |
| total number of replicating features | 8350 | 8472 | 8612 | 7973 |
| % replicating features (>2/3) | 83.9% | 81.0% | 81.3% | 79.9% |
| # detected known-unknowns | 5494 | 4103 | 5248 | 4444 |
| % variant unique detections | 34.2% | 51.6% | 39.1% | 44.3% |

Table 1 may provide an overview of the number and fraction of features detected in at least two out of three technical replicates, following co-detection across replicates and samples. as well as the "known-unknown" detection coverage for each of the individual *Passiflora* variants by using the above described search strategy. Note the higher number of features detected, which is a direct result of the use of reduced detection thresholds, aimed at increasing detection coverage, compared to the previously discussed MVA based profiling experiments. Technical feature detection replication was found to be similar, even slightly more favorable, compared to previous reported data and results, which is the direct result of a number feature detection limit setting during peak detection, thereby purposely limiting the detection of very low abundant, non-replicating features, with average replication values of approximately 80% for each of the individual variants. It was concluded however that the feature number limit however did not affect the analysis since replication values would have breached substantially higher replication values otherwise. Variant unique detections ranged from ~30% to 50% illustrating great chemical composition similarity across the four *Passiflora* variants. More importantly, this example illustrates that the detection and the required identification of non-variant specific compounds can be greatly reduced as "known-unknowns" do not have to be considered for analysis, which could be beneficial for not only natural products analysis, but a wide variety of applications, including food and environmental applications, such as authentication, profiling, speciation, food processing, ageing and storage, nutraceuticals, pharmaceutical applications, including, for instance, drug metabolism, pharmaceutical fingerprinting, biotransformation product analysis, and clinical applications, as applied in forensic toxicology for the detection of novel compounds, and/or the like. Embodiments are not limited in this context.

Figure 19:
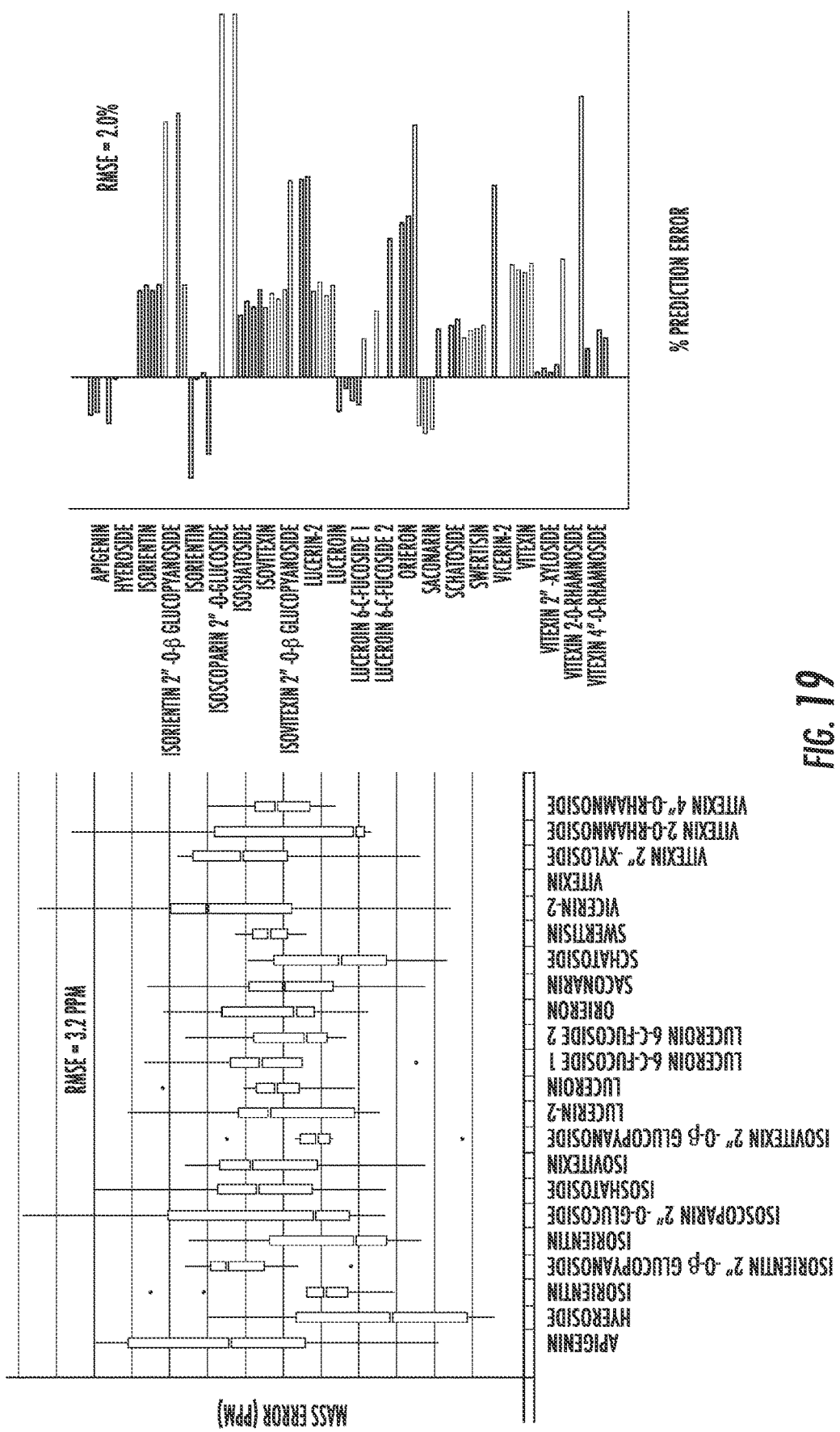

CCS prediction aided identification. Several common, well characterized *Passiflora* flavonoids were targeted to illustrate that the "known-unknown" complement of the LC-IM-MS data and can be annotated as known-knowns once compounds have been confidently identified. To aid the identification process, $^{TW}CCS_{N2}$ values were predicted (see, for example, Bouwmeester et al., "Predicting ion mobility collision cross sections by combining conventional and data driven modelling," *ASMS Proc.* MP 366 (2019)), thereby reducing the number of possibly isomeric species and spectra that had to be reviewed. The flavonoid compound target list and the obtained average results are summarized in the following Table 2:

surement error distributions together with root-mean standard errors (RMSE) values for the target compound set are shown in FIG. 19. In both cases, the majority of the compounds were detected within the expected error distributions ranges. Some prediction outliers were observed of which some of the O-linked species, i.e. β-glucopyranosides, showed interestingly the largest error, a (bio)chemical class of compounds that is less well-represented in the applied prediction model. However, in general, similar errors were observed across the variant in terms of abundance and direction, adding confidence to identification assignment of deconvoluted MS spectra. The utility of predictive CCS to aid retention time independent identification and known flavonoid elucidation is discussed in greater detail in the following section, describing how the confirmation of identification based on the observed product ion spectra has been performed, thereby enabling the output of machine learning predicted $^{TW}CCS_{N2}$ values to be gauged.

Tentative product ion spectrum annotation knownknowns (flavonoids) process. Natural product standard flavonoids may not always be available to perform IM-MS characterization and can be expensive to obtain. Herein, $^{TW}CCS_{N2}$ prediction has been explored as an alternative option and used to act as an effective identification parameter to reduce the number of isobaric and isomeric

TABLE 2

Table 3. Tentative identification and machine-learning based $^{TW}CCS_{N2}$ prediction results of literature reported endogenous *Passiflora* flavonoids.

| | | observed $t_r$ | # detected isomers[†] | | | | $^{TW}CCS_{N2}$ (Å$^2$) | | |
|---|---|---|---|---|---|---|---|---|---|
| | Δ ppm* | (min)** | E | A | C | I | predicted' | observed | variant |
| Apigenin° | 4.5 | 8.93 | 34 | 18 | 15 | 37 | 155.5 (−0.61) | 155.0 | EACI |
| Hyperoside | 3.0 | 8.30 | 18 | 8 | 6 | 10 | 199.3 (0.0) | 199.3 | AC |
| Isoorlentin° | 3.2 | 7.97 | 45 | 25 | 24 | 22 | 198.5 (−1.5) | 200.7 | EACI |
| Isoorientin 2"-O-β-glucopyranoside | 3.7 | 7.35 | 21 | 17 | 17 | 13 | 232.0 (−4.3) | 238.0 | EAI |
| Isosaponarin | 2.3 | 7.15 | 28 | 13 | 19 | 25 | 235.3 (−0.7) | 234.1 | EACI |
| Isoscoparin 2"-O-glucoside | 5.2 | 8.79 | 2 | 7 | 3 | 10 | 235.2 (−6.2) | 242.5 | CI |
| Isoshaftoside | 3.5 | 8.11 | 19 | 7 | 23 | 21 | 226.4 (−1.3) | 228.5 | EACI |
| Isovitexin" | 3.0 | 8.54 | 22 | 10 | 16 | 25 | 196.5 (−1.4) | 198.6 | EACI |
| Isovitexin 2"-O-β-glucopyraneside | 2.1 | 7.23 | 27 | 13 | 20 | 27 | 233.S (−3.3) | 239.7 | EAI |
| Lucenin-2° | 3.0 | 7.00 | 19 | 14 | 17 | 19 | 231.9 (−1.5) | 234.5 | EACI |
| Luteolin | 2.7 | 9.60 | 37 | 26 | 14 | 37 | 156.2 (−0.4) | 157.7 | EACI |
| Luteolin 6-C-fucoside 1 | 3.3 | 15.43 | 22 | 20 | 32 | 50 | 197.0 (−0.9) | 198.2 | EA |
| Luteoiin 5-C-fucoside 2 | 2.4 | 9.75 | 14 | 5 | 6 | 8 | 197.9 (−0.8) | 196.9 | EAI |
| Orientin° | 2.9 | 8.03 | 14 | 5 | 6 | 8 | 193.2 (−0.8) | 194.4 | EACI |
| Saponarin° | 2.5 | 7.83 | 28 | 13 | 19 | 25 | 236.9 (−0.8) | 238.5 | EACI |
| Schaftoside | 1.9 | 8.33 | 19 | 7 | 23 | 21 | 228.4 (−0.8) | 227.8 | EACI |
| Swertisin | 2.5 | 8.99 (7.55)[Δ] | 6 | 8 | 20 | 12 | 198.6 (−3.2) | 190.6 | C |
| Vicenin-2 | 4.6 | 7.49 | 27 | 17 | 8 | 31 | 231.5 (−1.9) | 234.6 | EACI |
| Vitexin* | 3.4 | 8.67 | 10 | 5 | 26 | 15 | 192.2 (−0.1) | 192.4 | EACI |
| Vitexin 2'-xyleside | 4.4 | 8.54 | 19 | 7 | 24 | 21 | 223.6 (−3.4) | 228.6 | AI |
| Vitexin 2-O-rharanoside | 2.5 | 8.67 | 23 | 13 | 10 | 24 | 226.3 (−0.7) | 227.4 | EAI |
| vitexin 4"-0-rhamnoside | — | — | — | — | — | — | 228.8 | — | — |

°compound (adduct specific) used to train machine-learning $^{TW}CCS_{N2}$ prediction model;
*root-mean-square error (RMSE) replicate injections and *Passiflora* variant samples;
**detected by predicted $^{TW}CCS_{N2}$ and CID MSn fragmentation interpretation;
[Δ]ambiguous detection;
[†] # (tentative) isomers detected determined by using 5 ppm, 10% $^{TW}CCS_{N2}$ and 10 min $t_r$ screening tolerances;
[†] mean absolute error (MAE) vs. observed $^{TW}CCS_{N2}$ in parenthesis;
— = not detected.

Figure 15:
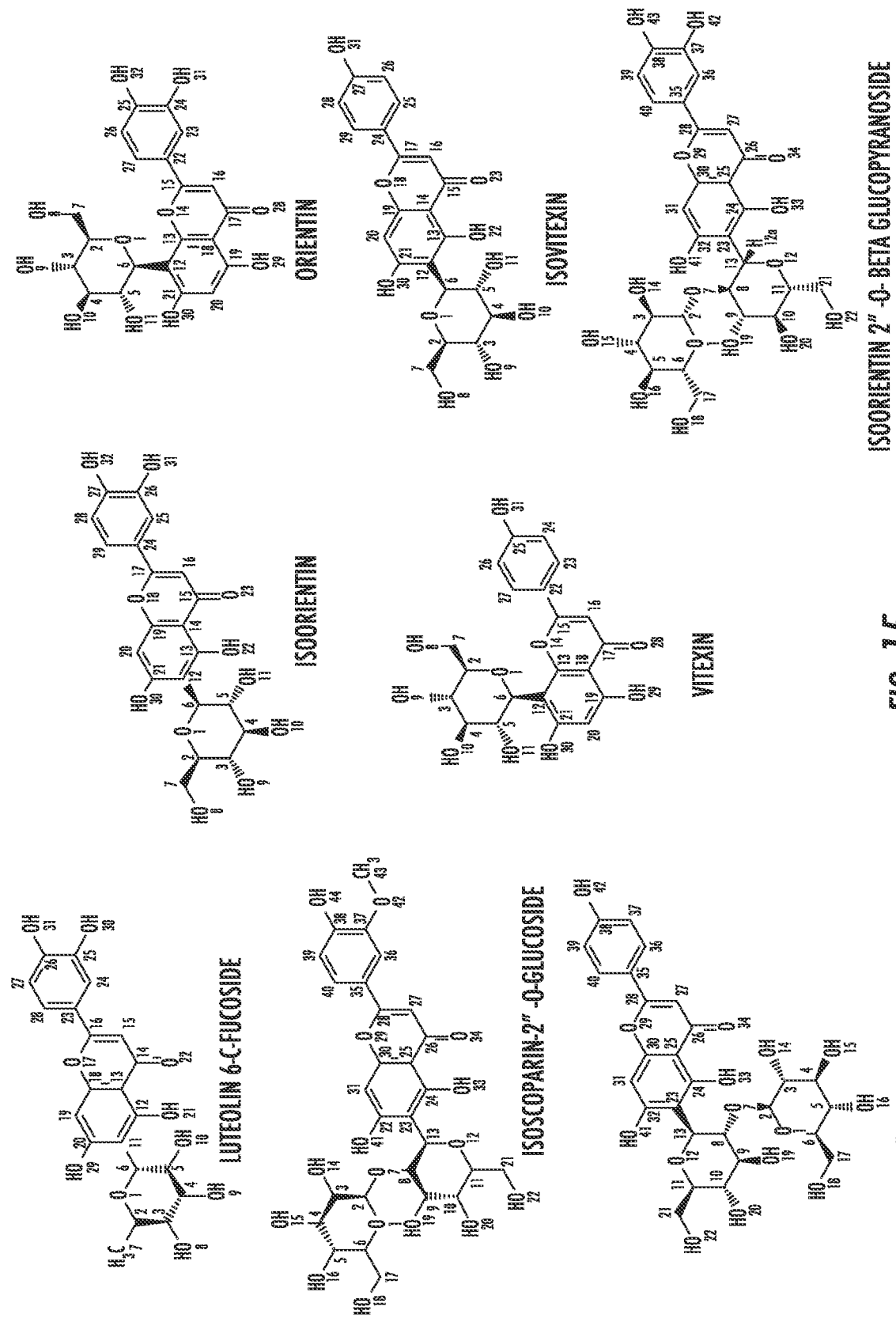
Figure 16:
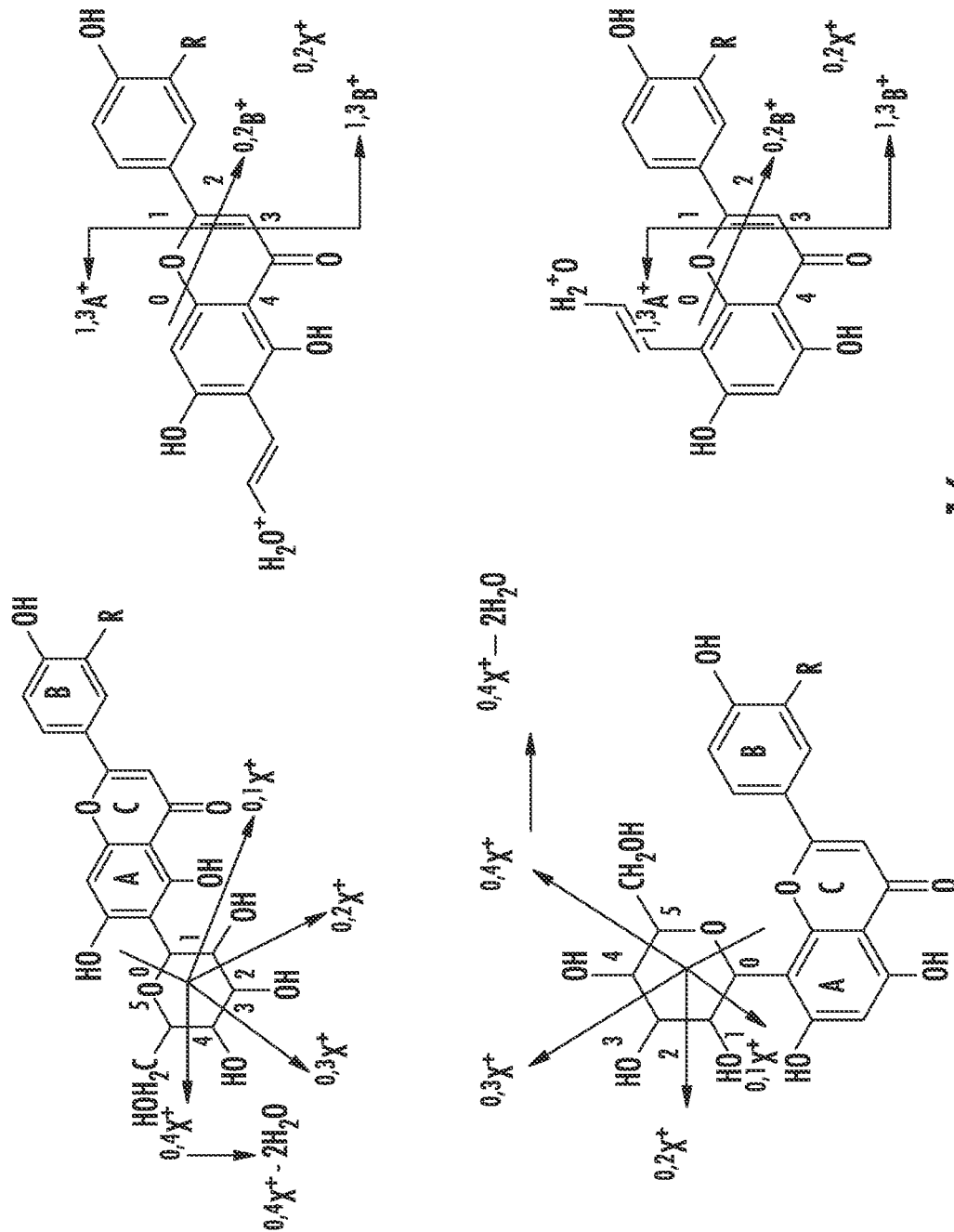
Figure 17:
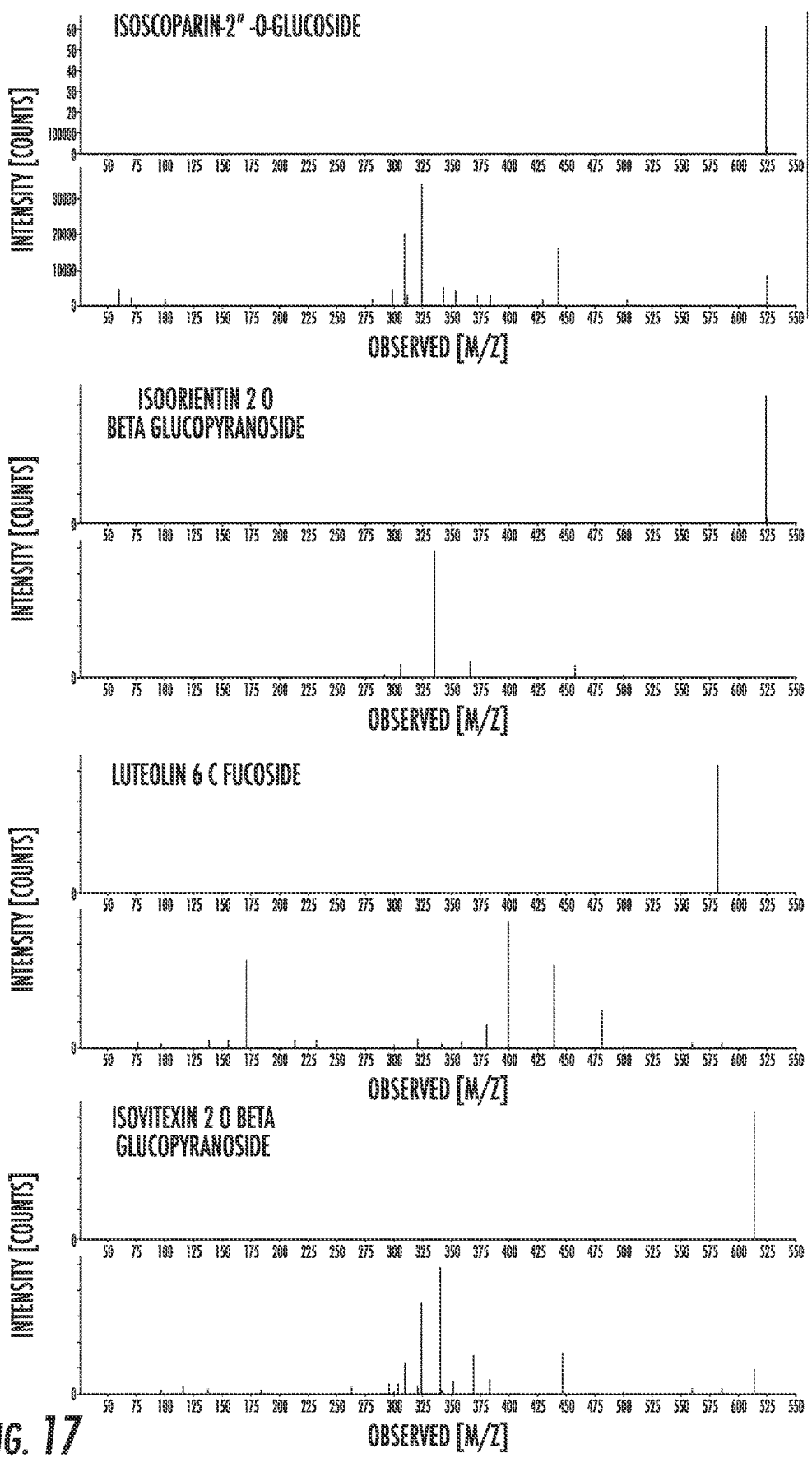
Figure 18:
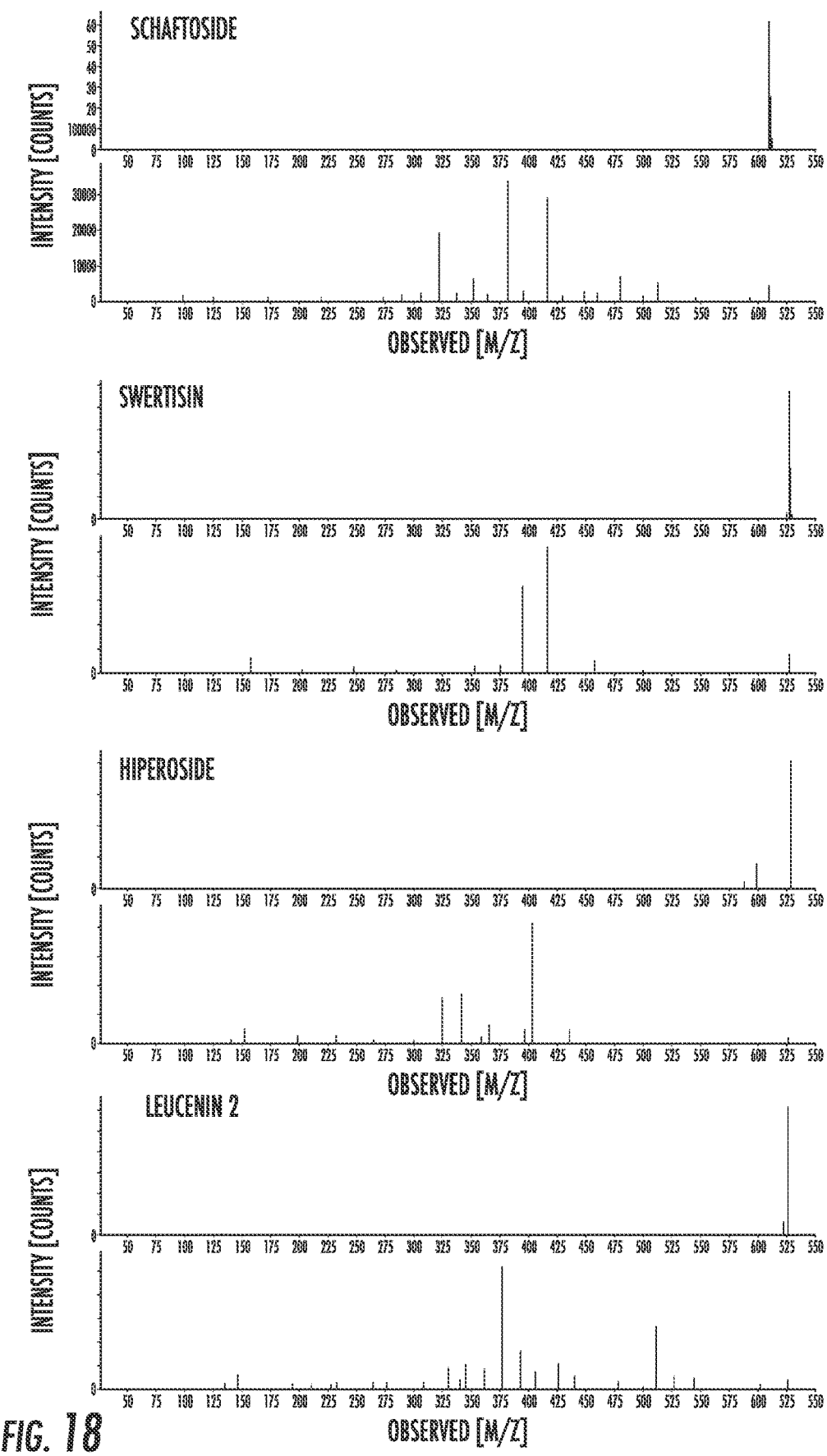

Example chemical structures and C 6/C 8 glycoside fragmentation pathways are provided in FIGS. 15 and 16, respectively. Some selected tentative identification examples are shown in FIGS. 17 and 18. The mass (observed vs. theoretical) and $^{TW}CCS_{N2}$ (observed vs. predicted) meaidentification of flavonoids reported to have been identified in *Passiflora* species. Retention time independent data processing, a 5 ppm accurate mass measurement tolerance, and a predicted vs. experimental 10% Å$^2$ ΔCCS tolerance were applied post peak detection to identify isobaric/isomeric species in the extracts of the four *Passiflora* species, enabling the retention time and the experimental $^{TW}CCS_{N2}$ values to be determined.

The number of isomeric species varied significantly with *Passiflora* species and the target flavonoid of interest. For example, in the case of isoorientin 2''-O-β glucopyranoside, between 13 and 21 isobaric species were observed and for isovitexin 2''-O-β glucopyranoside, the range was 13 to 27. IM also facilitates spectral complexity deconvolution in the analysis of medicinal plant/herbal remedy extracts and provides access to highly specific identification information. For isoorientin 2''-O-β glucopyranoside identified in *P. incarnata*, the retention time and drift time aligned product ion spectrum is shown in FIG. 17, which exhibits negative mode product ion abundance ratios at m/z 284/285, and m/z 297/298/299, characteristic of a 6-C diglycoside. This was also the case for isovitexin 2''-O-β glucopyranoside identified in *P. edulis*, which is shown in FIG. 17 as well. Isovitexin ($^{TW}CCS_{N2}$ 195.5 Å$^2$) and vitexin ($^{TW}CCS_{N2}$ 188.8 Å$^2$) are isomeric (sample elemental composition of $C_{21}H_{20}O_{10}$); hence, they are also observed at m/z 431. For m/z 431, within the four extracts, the number of retention time independent isobaric/isomeric species ranged between 10 and 28.

The Luteolin 6-C fucoside predicted $^{TW}CCS_{N2}$ values is 197.6 Å$^2$, which is similar to those predicted for 6-C glycoside isovitexin and isoorientin. However, as for 6-C glycoside isoorientin, Luteolin 6-C fucoside has hydroxyl groups at the C25/C26 position (isoorientin equivalent C26/C27), unlike isovitexin/vitexin, affording differentiation. The cleavage of the glucosyl group that forms a product ion at m/z 297 [M–H$^-$ 150]$^-$ is characteristic of a 6-C/8-C glycoside. The observed product ion abundance ratios at m/z 284/285, and m/z 297/298/299 confirm the identification of a 6-C glycoside. The observed CID spectrum is however not unlike that formed for isoorientin; however, a Luteolin 6-C-fucoside [M–H]$^-$ at m/z 431 precursor ion is observed due to absence of hydroxylation at the C7 position.

Isoscoparin-2''-O-glucoside m/z 443 [M–H]–180.0]$^-$ product ions are observed due to fragmentation of the diglycoside moiety and additionally m/z 297/298/299 product ions indicative of a 6-C glycoside were observed, providing further confirmation of identification. The number of isobaric species observed in the *Passiflora* extracts ranged between 2 and 10. The isomeric peaks at [M–H]$^-$ m/z 563 at $t_r$ 8.11 and 8.33 min exhibit non differential CID spectra assigned to schaftoside and isoschaftoside, respectively. Additionally, these isomers are not distinguished from each other using either predicted $^{TW}CCS_{N2}$ or measured values but are solely differentiated from other observed retention time independent isomeric species. Differentiation can however be determined from the resultant CID spectra. Both compounds formed a product ion at m/z 503.0, which is typical for asymmetric di-C-glycosides. Isoschaftoside and schaftoside can be characterized by the relative intensities of ion m/z 473 [M–H]–90]$^-$ and m/z 443 [M–H]–120.0]$^-$ product ions. Isochaftoside is characterized by intensity of m/z 473 [M–H]–90]$^-$<m/z 443 [M–H]–120]$^-$ and schaftoside by intensity m/z 473 [M–H]–90]$^-$>m/z 443 [M–H]–120]$^-$.

In the case of isoscoparin-2''-O-glucoside, m/z 443 [M–H]–180.0]$^-$ product ions are observed due to fragmentation of the diglycoside moiety. Also, the CID spectrum exhibits m/z 297/298/299 product ions, which are indicative of a 6-C glycoside, providing further confirmation of identification. The number of isobaric isoscoparin-2''-O-glucoside species observed in the *Passiflora* extracts ranged between 2 and 10. Here, the predicted $^{TW}CCS_{N2}$ value of 235.7 Å$^2$ differed by 6.2% from the experimental observed one. However, despite the relatively large difference in this particular example, as explained previously, predicted $^{TW}CCS_{N2}$ values have the potential to distinguish isomeric species from other isobaric and isomeric positional isomers without the requirement of analytical standards and retention time information.

Figure 20:
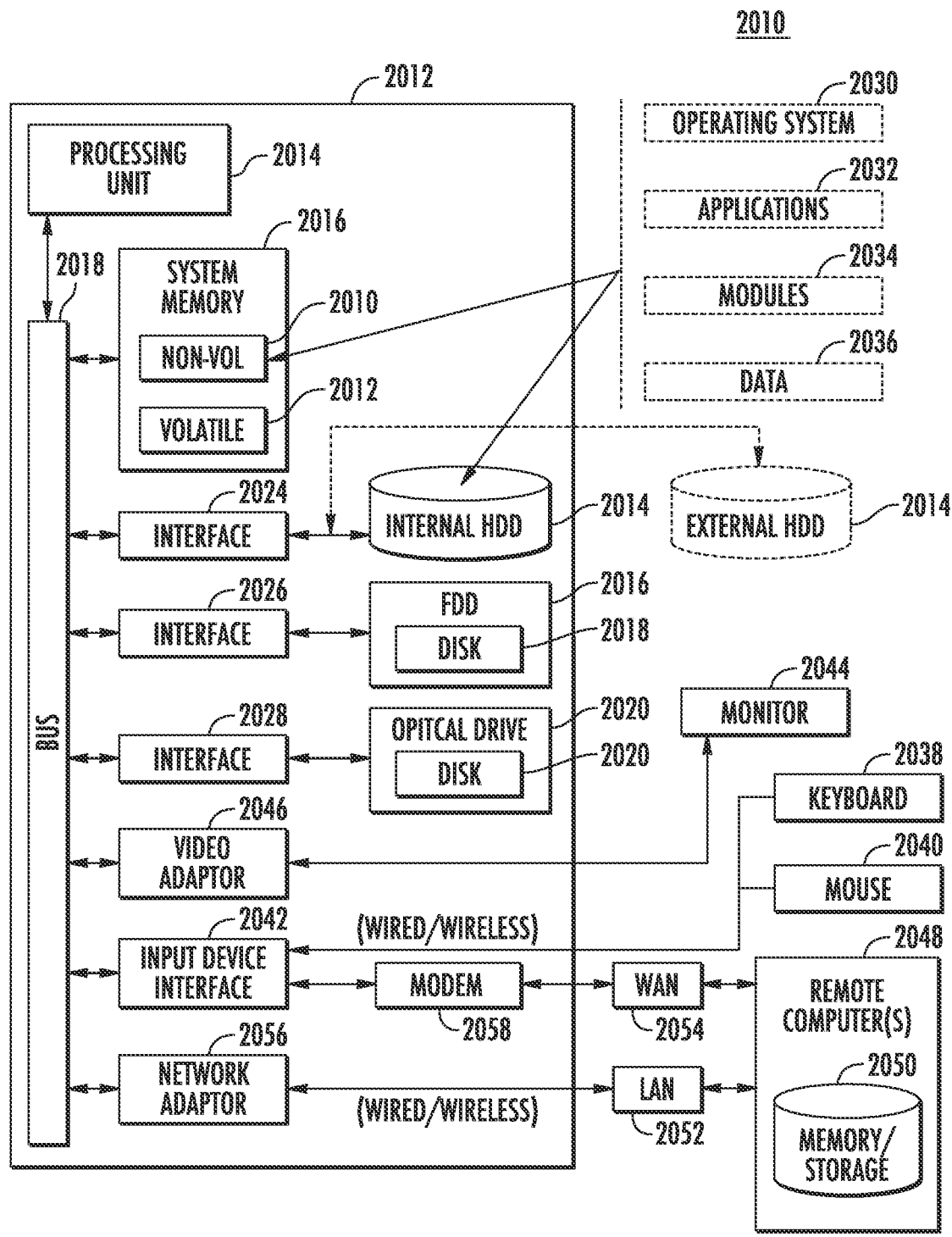
FIG. 20 illustrates an embodiment of a computing architecture.

FIG. 20 illustrates an embodiment of an exemplary computing architecture 2000 suitable for implementing various embodiments as previously described. In various embodiments, the computing architecture 2000 may comprise or be implemented as part of an electronic device. In some embodiments, the computing architecture 2000 may be representative, for example, of systems 205 and/or 305. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 2000. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 2000 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 2000.

As shown in FIG. 20, the computing architecture 2000 comprises a processing unit 2004, a system memory 2006 and a system bus 20020. The processing unit 2004 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 2004.

The system bus 20020 provides an interface for system components including, but not limited to, the system memory 2006 to the processing unit 2004. The system bus 20020 can be any of several types of bus structure that may further interconnect to a memory bus (with or without a memory controller), a peripheral bus, and a local bus using any of a variety of commercially available bus architectures. Interface adapters may connect to the system bus 2020 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 2006 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 20, the system memory 2006 can include non-volatile memory 20202010 and/or volatile memory 2012. A basic input/output system (BIOS) can be stored in the non-volatile memory 20202010.

The computer 2002 may include various types of computer-readable storage media in the form of one or more lower speed memory units, including an internal (or external) hard disk drive (HDD) 2014, a magnetic floppy disk drive (FDD) 2016 to read from or write to a removable magnetic disk 2019, and an optical disk drive 2020 to read from or write to a removable optical disk 2022 (e.g., a CD-ROM or DVD). The HDD 2014, FDD 2016 and optical disk drive 2020 can be connected to the system bus 20020 by a HDD interface 2024, an FDD interface 2026 and an optical drive interface 2020, respectively. The HDD interface 2024 for external drive implementations can include at least one or both of Universal Serial Bus (USB) and IEEE 1374 interface technologies.

The drives and associated computer-readable media provide volatile and/or nonvolatile storage of data, data structures, computer-executable instructions, and so forth. For example, a number of program modules can be stored in the drives and memory units 20202010, 2012, including an operating system 2030, one or more application programs 2032, other program modules 2034, and program data 2036. In one embodiment, the one or more application programs 2032, other program modules 2034, and program data 2036 can include, for example, the various applications and/or components according to some embodiments A user can enter commands and information into the computer 2002 through one or more wire/wireless input devices, for example, a keyboard 2038 and a pointing device, such as a mouse 2040. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 2004 through an input device interface 2042 that is coupled to the system bus 2008, but can be connected by other interfaces such as a parallel port, IEEE 1394 serial port, a game port, a USB port, an IR interface, and so forth.

A monitor 2044 or other type of display device is also connected to the system bus 20020 via an interface, such as a video adaptor 2046. The monitor 2044 may be internal or external to the computer 2002. In addition to the monitor 2044, a computer typically includes other peripheral output devices, such as speakers, printers, and so forth.

The computer 2002 may operate in a networked environment using logical connections via wire and/or wireless communications to one or more remote computers, such as a remote computer 2048. The remote computer 2002 can be a workstation, a server computer, a router, a personal computer, portable computer, microprocessor-based entertainment appliance, a peer device or other common network node, and typically includes many or all of the elements described relative to the computer 2002, although, for purposes of brevity, only a memory/storage device 2050 is illustrated. The logical connections depicted include wire/wireless connectivity to a local area network (LAN) 2052 and/or larger networks, for example, a wide area network (WAN) 2054. Such LAN and WAN networking environments are commonplace in offices and companies, and facilitate enterprise-wide computer networks, such as intranets, all of which may connect to a global communications network, for example, the Internet.

When used in a LAN networking environment, the computer 2002 is connected to the LAN 2052 through a wire and/or wireless communication network interface or adaptor 2056. The adaptor 2056 can facilitate wire and/or wireless communications to the LAN 2052, which may also include a wireless access point disposed thereon for communicating with the wireless functionality of the adaptor 2056.

When used in a WAN networking environment, the computer 2002 can include a modem 20520, or is connected to a communications server on the WAN 2054, or has other means for establishing communications over the WAN 2054, such as by way of the Internet. The modem 20520, which can be internal or external and a wire and/or wireless device, connects to the system bus 20020 via the input device interface 2042. In a networked environment, program modules depicted relative to the computer 2002, or portions thereof, can be stored in the remote memory/storage device 2050. It will be appreciated that the network connections shown are exemplary and other means of establishing a communications link between the computers can be used.

The computer 2002 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.\

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. An apparatus, comprising:
at least one memory; and
logic coupled to the at least one memory, the logic to:
receive analytical information for a plurality of product ions, the analytical information comprising product ion collision cross-section (CCS) information,
for at least one product ion of the plurality of product ions, determine a variance value of the product ion CCS information, and
determine that the analytical information comprises information for one or more of a plurality of substructural configurations or a plurality of isomers of the at least one product ion responsive to the variance value being over a variance threshold.

2. The apparatus of claim 1, the logic to exclude a candidate ion for the at least one product ion based on the product ion CCS information.

3. The apparatus of claim 1, the analytical information comprising a two-dimensional (2D) fingerprint of a product ion, the 2D fingerprint comprising product ion CCS information and mass-to-charge ratio (m/z) information.

4. The apparatus of claim 3, the logic to differentiate isomers of the plurality of product ions using the 2D fingerprint.

5. The apparatus of claim 1, the analytical information comprising a three-dimensional (3D) fingerprint of a product ion, the 3D fingerprint comprising product ion CCS information, intensity information, and mass-to-charge ratio (m/z) information.

6. The apparatus of claim 4, the logic to differentiate isomers of the plurality of product ions using the 3D fingerprint.

7. The apparatus of claim 1, the logic to:
receive historical product ion CCS information based on a priori structure determinations, and
exclude possible candidates for at least one product ion based on the product ion CCS information and the historical product ion CCS information.

8. A method, comprising:
receiving analytical information for a plurality of product ions, the analytical information comprising product ion collision cross-section (CCS) information;
determining, for at least one product ion of the plurality of product ions, a variance value of the product ion CCS information, and
determining that the analytical information comprises information for one or more of a plurality of substructural configurations or a plurality of isomers of the at least one product ion responsive to the variance value being over a variance threshold.

9. The method of claim 8, comprising excluding a candidate ion for the at least one product ion based on the product ion CCS information.

10. The method of claim 8, the analytical information comprising a two-dimensional (2D) fingerprint of a product ion, the 2D fingerprint comprising product ion CCS information and mass-to-charge ratio (m/z) information.

11. The method of claim 10, comprising differentiating isomers of the plurality of product ions using the 2D fingerprint.

12. The method of claim 8, the analytical information comprising a three-dimensional (3D) fingerprint of a product ion, the 3D fingerprint comprising product ion CCS information, intensity information, and mass-to-charge ratio (m/z) information.

13. The method of claim 12, comprising differentiating isomers of the plurality of product ions using the 3D fingerprint.

14. The method of claim 8, comprising:
receiving historical product ion CCS information based on a priori structure determinations; and
excluding possible candidates for at least one product ion based on the product ion CCS information and the historical product ion CCS information.

* * * * *